US009216193B2

(12) United States Patent
Hashimoto et al.

(10) Patent No.: US 9,216,193 B2
(45) Date of Patent: Dec. 22, 2015

(54) CROSSLINKED HYALURONIC ACID COMPOSITION AND SELF-CROSSLINKING HYALURONIC ACID PARTICLES

(75) Inventors: Masamichi Hashimoto, Machida (JP); Tadashi Morikawa, Chuo-ku (JP); Yoshiaki Miyata, Chuo-ku (JP); Akio Ohno, Machida (JP); Kei Takahashi, Machida (JP); Daisuke Ogasawara, Machida (JP); Kenji Fujii, Machida (JP); Teruaki Kakema, Machida (JP); Mariko Takeda, Machida (JP)

(73) Assignee: DENKI KAGAKU KOGYO KABUSHIKI KAISHA, Tokyo (JP)

( * ) Notice: Subject to any disclaimer, the term of this patent is extended or adjusted under 35 U.S.C. 154(b) by 375 days.

(21) Appl. No.: 13/818,848

(22) PCT Filed: Aug. 23, 2011

(86) PCT No.: PCT/JP2011/068978
§ 371 (c)(1),
(2), (4) Date: Apr. 23, 2013

(87) PCT Pub. No.: WO2012/026468
PCT Pub. Date: Mar. 1, 2012

(65) Prior Publication Data
US 2013/0203697 A1 Aug. 8, 2013

(30) Foreign Application Priority Data

Aug. 23, 2010 (JP) .................................. 2010-186487
Aug. 23, 2010 (JP) .................................. 2010-186491

(51) Int. Cl.
| | |
|---|---|
| *A61K 31/727* | (2006.01) |
| *A61K 31/728* | (2006.01) |
| *C08B 37/08* | (2006.01) |
| *C08L 5/08* | (2006.01) |
| *A61K 8/73* | (2006.01) |
| *A61K 9/00* | (2006.01) |

(52) U.S. Cl.
CPC ............... *A61K 31/728* (2013.01); *A61K 8/735* (2013.01); *A61K 9/0019* (2013.01); *A61K 9/0024* (2013.01); *C08B 37/0072* (2013.01); *C08L 5/08* (2013.01); *Y10T 428/2982* (2015.01)

(58) Field of Classification Search
CPC ...... C08B 37/0072; C08L 5/08; A61K 8/735; A61K 31/728
USPC .......................................................... 514/56
See application file for complete search history.

(56) References Cited

U.S. PATENT DOCUMENTS

| | | | |
|---|---|---|---|
| 2006/0040894 A1* | 2/2006 | Hunter et al. | 514/54 |
| 2006/0135469 A1 | 6/2006 | Miyata et al. | |
| 2008/0132585 A1* | 6/2008 | Miyata et al. | 514/777 |

FOREIGN PATENT DOCUMENTS

| | | |
|---|---|---|
| CN | 1649604 A | 8/2005 |
| JP | 63-123392 A | 5/1988 |
| JP | 2-234689 A | 9/1990 |
| JP | 2004-149599 A | 5/2004 |
| JP | 2004-181121 A | 7/2004 |
| JP | 2008-526747 A | 7/2008 |
| WO | WO 2004/016275 A1 | 2/2004 |

OTHER PUBLICATIONS

Bryant, S.J., Anseth, K.S. (2005) Photopolymerization of Hydrogel Scaffolds' in Scaffolding in Tissue Engineering, p. 71-90. Edited by Peter X. Ma and Jennifer Elisseeff. Published by CRC Press.*
Tezel, A., Fredrickson, G.H. (2008) The science of hyaluronic acid dermal fillers. Journal of Cosmetic and Laser Therapy, vol. 10, p. 35-42.*
Combined Chinese Office Action and Search Report issued Jan. 21, 2014 in Patent Application No. 201180046194.3 with English Translation of Category of Cited Documents.
International Search Report issued Oct. 11, 2011 in PCT/JP2011/068978.
English Translation of the International Preliminary Report on Patentability issued Mar. 28, 2013 in PCT/JP2011/068978.
English Translation of the Written Opinion of the International Searching Authority issued Oct. 11, 2011 in PCT/JP2011/068978.
M. Mihara et al., "Different Effects of High Molecular Weight Sodium Hyaluronate and NSAID on the Progression of the Cartilage Degeneration in Rabbit OA Model", Osteoarthritis and Cartilage, vol. 15, No. 5, 2007, pp. 543-549.
Toshiyuki Kikuchi et al., "Effect of High Molecular Weight Hyaluronan on Cartilage Degeneration in a Rabbit Model of Osteoarthritis", Osteoarthritis and Cartilage, vol. 4, No. 2, 1996, pp. 99-110.
Toshiyuki Kikuchi et al., "Effect of Hyaluronan on Cartilage Degeneration in Rabbit OA Model—Quantitative Analysis Using Scanning Electron Microscopy", Journal of Joint Surgery, vol. 15, No. 11, 1996, pp. 92-98 (with Partial English Translation).

(Continued)

*Primary Examiner* — Scarlett Goon
(74) *Attorney, Agent, or Firm* — Oblon, McClelland, Maier & Neustadt, L.L.P.

(57) ABSTRACT

The present invention provides a crosslinked hyaluronic acid composition including self-crosslinking hyaluronic acid particles having an equilibrium swelling capacity of 3-fold to 10-fold, and an aqueous solvent, wherein a dry weight of the self-crosslinking hyaluronic acid particles based on the total volume of the crosslinked hyaluronic acid composition is 3 w/v % to 8 w/v %.
The crosslinked hyaluronic acid composition of the invention uses self-crosslinking hyaluronic acid particles of which the equilibrium swelling capacity is within the above predetermined range. Accordingly, the viscosity does not sharply increase even if the concentration thereof is increased. Therefore, if the crosslinked hyaluronic acid composition is applied to an injection, it is possible to obtain a sufficient curative effect on knee osteoarthritis even with a small frequency of administration.

14 Claims, 17 Drawing Sheets

(56) References Cited

OTHER PUBLICATIONS

Chiaki Tateda et al., "Pharmacological Study on Drug Efficacy of Sodium Hyaluronate Preparation (ME3710) in Experimental Osteoarthritis (OA) and Fixed Joint Spasticity (PS) Rabbit Models", Japanese Pharmacology & Therapeutics, vol. 23, No. 4, 1995, pp. 833-841 (with Partial English Translation).

Hiromi Nochi et al., "Bioequivalence Test of New High-molecular-weight Hyaluronan Preparation That Can be Stored at Room Temperature", Japanese Pharmacology & Therapeutics, vol. 33, No. 4, 2005, pp. 303-312 (with English Abstract).

Kohji Watanabe et al., "Effect of High Molecular Weight Hyaluronic Acid on Fixed Joint", Orthopedic Research Science, vol. 9, 1982, pp. 77-79 (with Partial English Translation).

Kyosuke Miyazaki et al., "Effect of Sodium Hyaluronate on Fixed Joint in Rabbit", Orthopedic Research Science, vol. 11, 1984, pp. 125-127 (with Partial English Translation).

Tsutomu Kawano et al., "Mechanical Effects of the Intraarticular Administration of High Molecular Weight Hyaluronic Acid Plus Phospholipid on Synovial Joint Lubrication and Prevention of Articular Cartilage Degeneration in Experimental Osteoarthritis", Arthritis & Rheumatism, vol. 48, No. 7, Jul. 2003, pp. 1923-1929.

* cited by examiner

CROSSLINKED HYALURONIC ACID COMPOSITION AND SELF-CROSSLINKING HYALURONIC ACID PARTICLES

CROSS-REFERENCE TO RELATED APPLICATIONS

This application is a National Stage of PCT/JP2011/068978 filed Aug. 23, 2011. This application is based upon and claims the benefit of priority to Japanese Application No. 2010-186487 filed Aug. 23, 2010, and Japanese Application No. 2010-186491 file Aug. 23, 2010.

TECHNICAL FIELD

The present invention relates to a crosslinked hyaluronic acid composition, self-crosslinking hyaluronic acid particles used for the composition, an injection containing the crosslinked hyaluronic acid composition, and a prefilled syringe formulation containing the injection.

BACKGROUND ART

Hyaluronic acid is linear polymeric polysaccharide in which β-D-N-acetylglucosamine and β-D-glucuronic acid alternatively bind to each other. Showing excellent biocompatibility and viscoelasticity, the hyaluronic acid is increasingly applied to medical uses. As one of the uses, Patent Literature 1 discloses the use of hyaluronic acid crosslinked as a viscosity replenisher for knee osteoarthritis.

CITATION LIST

Patent Literature

[Patent Literature 1] PCT Japanese Translation Patent Publication No. 2008-526747

SUMMARY OF INVENTION

Technical Problem

However, when being injected into the joint region suffering from knee osteoarthritis, the hyaluronic acid needs to be administered several times to 10 times to obtain a resultful curative effect, and this puts a heavy burden on patients.

In this respect, an object of the invention is to provide a crosslinked hyaluronic acid composition which can produce a sufficient curative effect for knee osteoarthritis even when the frequency of administration thereof is reduced compared to the related art, and self-crosslinking hyaluronic acid particles used for the composition.

Solution to Problem

The invention provides a crosslinked hyaluronic acid composition containing: self-crosslinking hyaluronic acid particles having an equilibrium swelling capacity of 3-fold to 10-fold; and an aqueous solvent, wherein a dry weight of the self-crosslinking hyaluronic acid particles based on the total volume of the crosslinked hyaluronic acid composition is 3 w/v % to 8 w/v %.

When an injection for knee osteoarthritis is produced using hyaluronic acid or crosslinked hyaluronic acid known in the related art, if the concentration of the hyaluronic acid or crosslinked hyaluronic acid is increased (for example, 3 w/v % to 8 w/v % as a dry weight) to reduce the frequency of administration, the viscosity increases sharply, so it is extremely difficult to inject the injection into an affected area from a syringe. On the other hand, in order to make it easy to inject the injection from a syringe, the molecular weight or concentration of the hyaluronic acid or the crosslinked hyaluronic acid should be reduced, so a sufficient curative effect on knee osteoarthritis cannot be obtained with a small frequency of administration.

In the invention, since the self-crosslinking hyaluronic acid particles having an equilibrium swelling capacity within the above predetermined range are used, the viscosity does not sharply increase even if the concentration thereof is increased. Accordingly, when the crosslinked hyaluronic acid composition is applied to an injection, it is possible to obtain a sufficient curative effect on knee osteoarthritis even with a small frequency of administration.

In the crosslinked hyaluronic acid composition of the invention, an average volume particle size of the self-crosslinking hyaluronic acid particles is preferably 10 μm to 100 μm. If the self-crosslinking hyaluronic acid particles having the average volume particle size and the equilibrium swelling capacity within the above predetermined range are used, the viscosity does not sharply increase even if the concentration thereof is increased. Accordingly, when the crosslinked hyaluronic acid composition is applied to an injection, it is possible to obtain a sufficient curative effect on knee osteoarthritis even with a small frequency of administration.

In the crosslinked hyaluronic acid composition of the invention that has the average volume particle size and the equilibrium swelling capacity within the above predetermined range, a degree of self-crosslinking esterification of the self-crosslinking hyaluronic acid particles is preferably 0.05 mol % to 0.50 mol %. In addition, the self-crosslinking hyaluronic acid particles include of self-crosslinking hyaluronic acid crosslinked by ester bonds that are easily hydrolyzed under in-vivo conditions. When the ester bond is hydrolyzed, molecular hyaluronic acid is generated. The molecular weight (defined as a primary molecular weight and described as a viscosity average molecular weight) of the hyaluronic acid generated by hydrolysis is preferably 800,000 or more in view of the curative effect thereof.

Moreover, in the crosslinked hyaluronic acid composition of the invention, the self-crosslinking hyaluronic acid particles preferably contains ethyl ester in an amount of 0.05 mol % or less and have a degree of self-crosslinking esterification of 0.05 mol % to 0.50 mol %. If the self-crosslinking hyaluronic acid particles in which the amount of ethyl ester, the degree of self-crosslinking esterification, and the equilibrium swelling capacity are within the above predetermined range are used, the viscosity does not sharply increase even if the concentration thereof is increased. Accordingly, when the crosslinked hyaluronic acid composition is applied to an injection, it is possible to obtain a sufficient curative effect on knee osteoarthritis even with a small frequency of administration.

In the crosslinked hyaluronic acid composition of the invention in which the amount of the ethyl ester, the degree of self-crosslinking esterification, and the equilibrium swelling capacity are within the above predetermined range, the self-crosslinking hyaluronic acid particles include of self-crosslinking hyaluronic acid crosslinked by ester bonds that are easily hydrolyzed under in-vivo conditions. When the ester bond is hydrolyzed, molecular hyaluronic acid is generated. The molecular weight (defined as a primary molecular weight and described as a viscosity average molecular weight) of the hyaluronic acid generated by hydrolysis is preferably 800,000 or more in view of the curative effect thereof.

If the self-crosslinking hyaluronic acid particles having an average volume particle size of 10 μm to 100 μm, an equilibrium swelling capacity of 3-fold to 10-fold, a primary molecular weight of 800,000 or more, and a degree of self-crosslinking esterification of 0.05 mol % to 0.50 mol % is used, or, if the self-crosslinking hyaluronic acid particles containing ethyl ester in an amount of 0.05 mol % or less and having a degree of self-crosslinking esterification of 0.05 mol % to 0.50 mol %, an equilibrium swelling capacity of 3-fold to 10-fold, and a primary molecular weight of 800,000 or more is used, the frequency of administration is further reduced, and the curative effect on knee osteoarthritis becomes more apparent. For example, if such particles are dipped in 10 mM phosphate-buffered physiological saline at pH of 7.0±0.5 and a temperature of 36.0±2.0° C., the crosslinked hyaluronic acid can completely dissolve within 30 days. At this time, hyaluronic acid having a sufficiently high molecular weight can be generated, so a potent curative effect can be obtained from the hyaluronic acid. Moreover, it is possible to adjust the viscosity, which is measured at 25±2° C. and a shearing speed of 50 $S^{-1}$ by rotational viscometry using a cone and plate, to be 300 mPa·s or less, so the hyaluronic acid can be easily injected as an injection.

The invention provides an injection containing the crosslinked hyaluronic acid composition. As described above, when the hyaluronic acid concentration is increased to 3 w/v % to 8 w/v % in a hyaluronic acid-based injection of the related art, the viscosity increases sharply, which makes it extremely difficult to inject the injection into an affected area from a syringe. However, since the injection according to the invention uses the crosslinked hyaluronic acid composition containing the self-crosslinking hyaluronic acid particles having the above predetermined physical properties, it is possible to obtain a sufficient curative effect on knee osteoarthritis even with a small frequency of administration.

The invention provides an injection which is used such that the crosslinked hyaluronic acid is administered at 1.25 mg/kg body weight or a higher dose per administration, or an injection which is used such that 75 mg or more of the crosslinked hyaluronic acid is administered per administration. As described above, if the hyaluronic acid concentration is high in the hyaluronic acid-based injection of the related art, the viscosity increases sharply, which makes it difficult to inject the injection into an affected area from a syringe. Consequently, the hyaluronic acid in such an amount that can produce a sufficient curative effect cannot be given by a single administration. However, since the injection according to the invention uses the crosslinked hyaluronic acid composition containing the self-crosslinking hyaluronic acid particles having the above physical properties, the injection can be used such that the crosslinked hyaluronic acid is administered at 1.25 mg/kg body weight or a higher dose per administration or 75 mg or more of the crosslinked hyaluronic acid is administered per administration. Accordingly, it is possible to obtain a sufficient curative effect on knee osteoarthritis even by a single administration.

The invention provides a prefilled syringe formulation containing the above injection. In a prefilled syringe formulation containing the hyaluronic acid-based injection of the related art, if the hyaluronic acid concentration is increased (for example, 3 w/v % to 8 w/v %) as described above, the viscosity increases sharply. Accordingly, it is difficult to inject the injection into an affected area from the syringe. However, in the prefilled syringe formulation according to the invention, the crosslinked hyaluronic acid composition containing the self-crosslinking hyaluronic acid particles having the above predetermined physical properties is contained as an injection inside a syringe barrel. Therefore, it is possible to obtain a sufficient curative effect on knee osteoarthritis even with a small frequency of administration.

In addition, the invention provides self-crosslinking hyaluronic acid particles having an average volume particle size of 10 μm to 100 μm and an equilibrium swelling capacity of 3-fold to 10-fold. If a crosslinked hyaluronic acid composition containing the self-crosslinking hyaluronic acid particles having the above predetermined physical properties is applied to an injection, the viscosity does not sharply increase even if the hyaluronic acid concentration is increased to 3 w/v % to 8 w/v %. Accordingly, it is possible to obtain a sufficient curative effect on knee osteoarthritis even with a small frequency of administration.

The self-crosslinking hyaluronic acid particles of the invention that have the average volume particle size and the equilibrium swelling capacity within the above predetermined range preferably has a primary molecular weight of 800,000 or more and a degree of self-crosslinking esterification of 0.05 mol % to 0.50 mol %. If such self-crosslinking hyaluronic acid particles are used, the frequency of administration is further reduced, and the curative effective on knee osteoarthritis becomes more apparent.

The invention also provides self-crosslinking hyaluronic acid particles containing ethyl ester in an amount of 0.05 mol % or less and having a degree of self-crosslinking esterification of 0.05 mol % to 0.50 mol % and an equilibrium swelling capacity of 3-fold to 10-fold. When a crosslinked hyaluronic acid composition containing the self-crosslinking hyaluronic acid particles having the above predetermined physical properties is applied to an injection, the viscosity does not sharply increase even if the hyaluronic acid concentration is increased to 3 w/v % to 8 w/v %. Accordingly, it is possible to obtain a sufficient curative effect on knee osteoarthritis even with a small frequency of administration.

The self-crosslinking hyaluronic acid particles of the invention in which the amount of ethyl ester, the degree of self-crosslinking esterification, and the equilibrium swelling capacity are within the above predetermined range preferably have a primary molecular weight of 800,000 or more. If such self-crosslinking hyaluronic acid particles are used, the frequency of administration is further reduced, and the curative effect on knee osteoarthritis becomes more apparent.

Advantageous Effects of Invention

According to the invention, it is possible to provide a crosslinked hyaluronic acid composition which can produce a sufficient curative effect on knee osteoarthritis even if the frequency of administration thereof is reduced compared to the related art, and self-crosslinking hyaluronic acid particles used for the composition.

DESCRIPTION OF EMBODIMENTS

Figure 1:
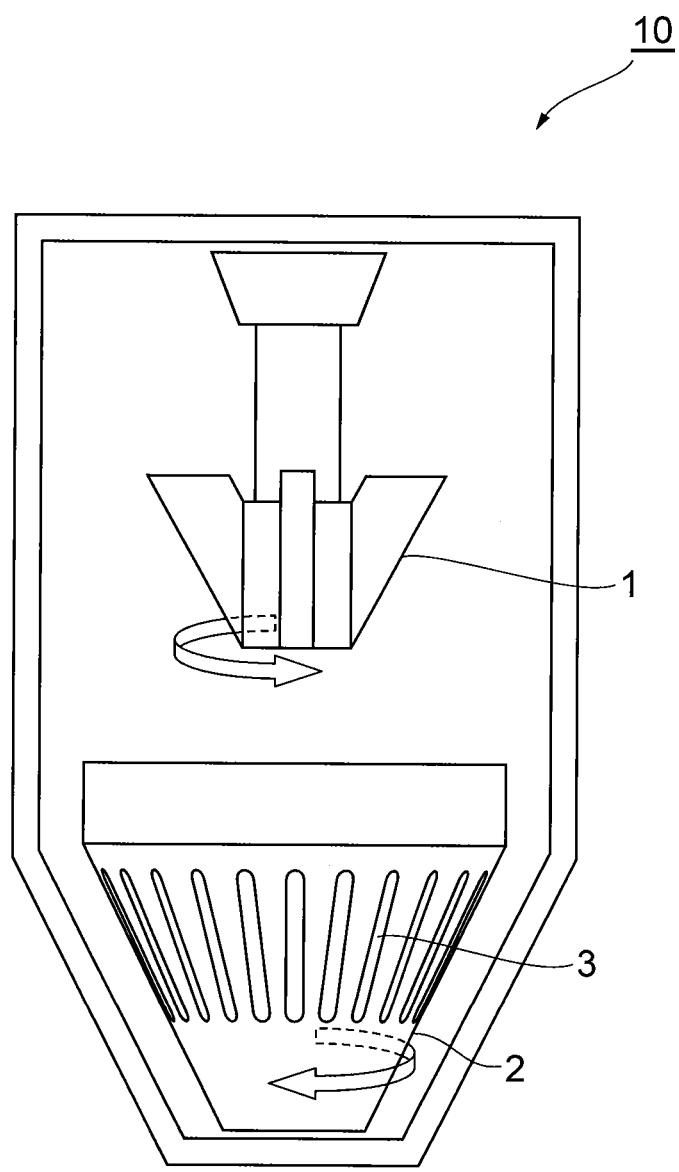
FIG. 1 is a schematic configuration view of a high-speed rotation device that is used for producing self-crosslinking hyaluronic acid particles according to the invention.

Hereinafter, preferable embodiments of the invention will be described.

The crosslinked hyaluronic acid composition according to the first embodiment of the invention contains self-crosslinking hyaluronic acid particles having an average volume particle size of 10 μm to 100 μm and an equilibrium swelling capacity of 3-fold to 10-fold.

In addition, the crosslinked hyaluronic acid composition according to the second embodiment of the invention contains self-crosslinking hyaluronic acid particles which contain ethyl ester in an amount of 0.05 mol % or less and have a self-crosslinking estrification degree of 0.05 mol % to 0.50 mol % and an equilibrium swelling capacity of 3-fold to 10-fold.

In the invention, the self-crosslinking hyaluronic acid particles refer to granulated self-crosslinking hyaluronic acid. Herein, the self-crosslinking hyaluronic acid refers to hyaluronic acid having a crosslinked structure, in which a portion of carboxylic groups in hyaluronic acid molecules forms an ester bond for itself with a hydroxyl group of the same and/or another hyaluronic acid molecule to form a three-dimensional network structure. The self-crosslinking hyaluronic acid does not include those using a chemical crosslinking agent or a chemical modifier.

The degree of self-crosslinking esterification of the self-crosslinking hyaluronic acid particles refers to a ratio, which is expressed as mol %, of an integral value of peaks of chemical shift derived from crosslinked ester to an integral value of peaks of chemical shift derived from the main chain structure of hyaluronic acid.

The self-crosslinking estrification degree of the self-crosslinking hyaluronic acid particles according to the first embodiment of the invention is preferably 0.05 mol % to 0.50 mol % and more preferably 0.08 mol % to 0.30 mol %. Moreover, the degree of self-crosslinking esterification of the self-crosslinking hyaluronic acid particles according to the second embodiment of the invention is 0.05 mol % to 0.50 mol % and preferably 0.08 mol % to 0.30 mol %.

For measuring the degree of self-crosslinking esterification, it is necessary to lower the molecular weight of the hyaluronic acid beforehand by hydrolyzing the main chain of the hyaluronic acid. At this time, it is necessary to inhibit the hydrolysis of the self-crosslinking ester bond. Accordingly, hydrolysis treatment is performed using a hyaluronic acid hydrolase for selectively hydrolyzing only the main chain structure of the self-crosslinking hyaluronic acid, and an integral value of peaks of chemical shift is measured by proton nuclear magnetic resonance (NMR). Specifically, an area ratio of the peak corresponding to an ester-crosslinked portion (4.18 ppm) to the peak corresponding to an acetyl methyl group (2.05 ppm) is calculated as the degree of self-crosslinking esterification.

The amount of ethyl ester in the self-crosslinking hyaluronic acid particles according to the first embodiment of the invention is preferably 0.05 mol % or less. Moreover, the amount of ethyl ester in the self-crosslinking hyaluronic acid particles according to the second embodiment of the invention is preferably 0.05 mol % or less. The amount of ethyl ester is the content of ethyl ester contained in the self-crosslinking hyaluronic acid particles and is considered to be yielded by ethyl estrification of ethanol contained as a residual solvent in a raw material of hyaluronic acid.

However, ethyl ester is considered to hinder self-esterification. Therefore, if ethanol contained in the raw material of hyaluronic acid is removed by being subjected to freeze vacuum drying, exposed to air at 80° C., and washed with acetone or exposed to air at room temperature for 2 to 3 days, the amount of ethyl ester in the self-crosslinking hyaluronic acid particles can be adjusted to 0.05 mol % or less. The content of ethanol contained in the raw material of hyaluronic acid can be measured by gas chromatography/mass spectrometry (GC-MS) by extraction using acetonitrile.

The amount of ethyl ester in the self-crosslinking hyaluronic acid particles is preferably 0.03 mol % or less. The amount of ethyl ester can be measured by NMR similarly to the degree of self-crosslinking esterification.

In the invention, as the hyaluronic acid, those extracted from animal tissues or produced by zymotechnics can be used regardless of the source.

As strains used in the zymotechnics, microorganisms having an ability to produce hyaluronic acid, such as the genus Streptococcus isolated from nature, or mutants stably producing hyaluronic acid with a high yield, such as Streptococcus equi FM-100 (FERM 9027) disclosed in Japanese Unexamined Patent Application Publication No. 63-123392 and Streptococcus equi FM-300 (FERM 2319) disclosed in Japanese Unexamined Patent Application Publication No. 2-234689, are desirable. The hyaluronic acid cultured using the above mutant and purified is used.

In addition, the concept of the hyaluronic acid used includes alkali salts thereof, for example, salts of sodium, potassium, or lithium.

The self-crosslinking hyaluronic acid is obtained by allowing hyaluronic acid to coexist with water for adjusting the hyaluronic acid concentration to 5% by mass or more and an acid component of moles equal to or more than that of a carboxyl group of the hyaluronic acid, and maintaining the state of coexistence at a low temperature.

The acid allowed to coexist with the hyaluronic acid is not particularly limited, and any known acid can be used. However, the acid is preferably an acid stronger than the hyaluronic acid, and more preferably an inorganic acid. The acid is even more preferably hydrochloric acid, nitric acid, or sulfuric acid, and among these, nitric acid which is excellent in handleability or the like is particularly preferable.

The amount of the acid allowed to coexist is not particularly limited, and can be set to be equal to or more than moles of a carboxyl group of the hyaluronic acid.

It is preferable that the hyaluronic acid and the acid allowed to be coexist be held in such an amount that the content of the hyaluronic acid becomes 15% by mass or more, preferably from 20% by mass to 40% by mass, based on the whole mixture. The hyaluronic acid and the acid allowed to coexist can be held at a temperature from −30° C. to 25° C. for any duration from 1 hour to 20 days. Particularly preferably, they can be held at a temperature from −25° C. to −5° C. for 1 day to 15 days. For mixing the hyaluronic acid with the acid allowed to coexist, the hyaluronic acid is kneaded with the acid allowed to coexist such that the amount of the hyaluronic acid becomes 15% by mass or more and more preferably 20% by mass or more based on the whole mixture, whereby it is possible to put the acid allowed to coexist in a uniform state. Moreover, it is possible to impregnate the hyaluronic acid with the acid allowed to coexist such that the amount thereof becomes 15% by mass or more and preferably 20% by mass or more based on the whole mixture. It is also possible to concentrate an aqueous acidic solution of the hyaluronic acid adjusted to a low concentration such that the content of the hyaluronic acid becomes 15% by mass or more and preferably 20% by mass or more based on the whole mixture.

The average volume particle size of the self-crosslinking hyaluronic acid particles according to the first embodiment of the invention is 10 μm to 100 μm, preferably 20 μm to 80 μm, and more preferably 40 μm to 70 μm. Moreover, the average volume particle size of the self-crosslinking hyaluronic acid particles according to the second embodiment of the invention is preferably 10 μm to 100 μm, more preferably 20 μm to 80 μm, and even more preferably 40 μm to 70 μm. If the average volume particle size of the self-crosslinking hyaluronic acid particles falls within the above range when the particles swell, and the equilibrium swelling capacity thereof is 3-fold to 10-fold, the viscosity does not sharply increase even if the concentration of the crosslinked hyaluronic acid composition is increased, and a more amount of the hyaluronic acid can be injected into the body.

The self-crosslinking hyaluronic acid particles are an aggregate of particles having various shapes and sizes. Accordingly, the average volume particle size thereof is measured by, for example, using a diameter of a circle, which has an area equivalent to a particle image projected when the particle is photographed, as an equivalent circle diameter. For example, about 10,000 particle images are analyzed to calculate the volume of spherical particles having the equivalent circle diameter as their diameter, and the values are added up from the value of particles having small volume. At this time, the equivalent circle diameter of particles at the point in time when the value reaches 50% of the sum of the volume of 10,000 particles can be employed as an average volume particle size. Specifically, for the measurement, for example, a particle size/shape distribution analyzer PITA-1 (trade name, manufactured by SEISHIN ENTERPRISE Co., Ltd.) can be used.

The self-crosslinking hyaluronic acid particles can be produced in a mariner in which a mixed solution of the self-crosslinking hyaluronic acid and an aqueous solvent is atomized by being passed through a slit, at a temperature of lower than 50° C. in a state of being applied with a shearing force. For example, if a high-speed rotation device which performs atomization by passing the mixture through a slit while applying a shearing force is used to crush the self-crosslinking hyaluronic acid, fine particles having an average volume particle size of 10 μm to 100 μm can be obtained. In addition, it is preferable to control a cooling temperature to be lower than 50° C. at the time of crushing, since the molecular weight of the produced self-crosslinking hyaluronic acid and the molecular weight of the hyaluronic acid eluted from the self-crosslinking hyaluronic acid can be kept high in this manner.

FIG. 1 is a schematic configuration view of a high-speed rotation device used for producing the self-crosslinking hyaluronic acid particles according to the invention. The high-speed rotation device 10 is provided with a rotor 1 and a screen 2. The rotor 1 and the screen 2 perform counter rotation, and the self-crosslinking hyaluronic acid passes through a slit 3 of the screen 2 so as to be atomized as self-crosslinking hyaluronic acid particles. In this manner, since the rotor 1 and the screen 2 perform counter rotation, a strong shearing force is obtained, whereby atomized self-crosslinking hyaluronic acid particles can be obtained. Moreover, presumably, when the high-speed rotation device 10 atomizes the self-crosslinking hyaluronic acid, the device can efficiently crush the particles without randomly cutting the main chain of hyaluronic acid constituting the fine particles, whereby self-crosslinking hyaluronic acid particles having a high molecular weight and a low viscosity can be obtained.

As such a high-speed rotation device, for example, Clearmix W Motion (trade name, manufactured by M Technique Co., Ltd.) is preferable. This device is constituted with a rotor rotating at a high speed and a screen disposed to surround the rotor. Due to a large velocity gradient near the surface of the rotor rotating at a high speed, a shearing force is applied to large particles of self-crosslinking hyaluronic acid passing through a liquid-passing hole (slit) of the screen, whereby the particles are atomized.

A degree of atomization performed by the high-speed rotation device is specified by the rotation speed of the rotor and the screen and the treatment time, as shown in Table 1. The ratio of the rotation speed of the screen to the rotation speed of the rotor is preferably 50% to 100% and particularly preferably 90%.

TABLE 1

| Treatment conditions | | Average volume particle size (μm) | |
|---|---|---|---|
| Rotation speed (rpm) | Treatment time (min) | Before treatment | After treatment |
| 10,000 | 20 | 500 to 1,000 | 90 to 130 |
| 17,000 | 30 | | 60 to 70 |
| 20,000 | 30 | | 45 to 60 |
| 20,000 | 120 | | 30 to 45 |

As a high-pressure crushing device, for example, there is Nanomizer (trade name, manufactured by NANOMIZER Inc.). However, in this device, the temperature of a sample exposed to a high pressure and high speed easily increases, and the physical properties of the self-crosslinking hyaluronic acid deteriorates to a large extent. Accordingly, it is not preferable to use the device in the atomizing treatment for the self-crosslinking hyaluronic acid particles according to the invention. Moreover, among high-speed rotation devices, it is not preferable to use a device that cannot make fine particles having an average volume particle size of 200 μm or less, for example, T. K. Homomix (trade name, manufactured by PRIMIX Corporation), in the atomizing treatment for the self-crosslinking hyaluronic acid particles according to the invention.

Herein, the term "deterioration of physical properties" means that the physical properties of the self-crosslinking hyaluronic acid before crushing, such as a half-life of solubility at 60° C. and a primary molecular weight, further deteriorate due to granulation (atomization) such as crushing, compared to the initial value obtained before crushing. It is preferable that the physical properties of the self-crosslinking hyaluronic acid particles obtained by the atomization treatment do not deteriorate if possible.

In addition, the term "half-life of solubility at 60° C." refers to the time taken for a gel fraction, which is 100% at the beginning, to become 50% when self-crosslinking hyaluronic acid is heated under conditions of 60° C. and pH 7.4. For example, the initial value of the half-life of solubility at 60° C. is 25 hours before granulation, but when the half-life after granulation is 20 hours, the initial value is maintained by 80%, which shows that the physical properties deteriorate by 20% due to granulation.

The gel fraction is a value, which is expressed as a percentage, of a proportion of the hyaluronic acid precipitated as self-crosslinking hyaluronic acid particles in the total amount of hyaluronic acid in the crosslinked hyaluronic acid composition. As shown in the following Formula (1), the gel fraction can be calculated by subtracting the amount of residual hyaluronic acid, which is generated when ester crosslinks are hydrolyzed, and released and dissolved as hyaluronic acid in a solvent, from the total amount of hyaluronic acid.

$$\text{Gel fraction (\%)} = (1 - (\text{amount of dissolved hyaluronic acid/total amount of hyaluronic acid})) \times 100 \quad (1)$$

The primary molecular weight of the self-crosslinking hyaluronic acid particles of the invention is a molecular weight of the hyaluronic acid generated by hydrolysis of ester bonds of the self-crosslinking hyaluronic acid particles. The primary molecular weight is preferably 800,000 or more, and more preferably in a range of 800,000 to 3,000,000. If the primary molecular weight is within the above range, both the self-crosslinking hyaluronic acid particles having a high molecular weight and self-crosslinking hyaluronic acid particles having a low molecular weight that are obtained by hydrolysis treatment or the like can be preferably used in the same manner.

The primary molecular weight can be expressed as a viscosity average molecular weight. The primary molecular weight can be calculated in a manner in which the crosslinking point of the self-crosslinking hyaluronic acid is cut and dissolved to obtain hyaluronic acid, a differential refractometer is then used as a detector for GPC, and the primary molecular weight is calculated from the retention time of a peak top of the molecular weight distribution. For calculating the viscosity average molecular weight from the retention time, a calibration curve is used which is created using the retention time of a peak top of the molecular weight distribution of hyaluronic acid of which the viscosity average molecular weight has already been known. In order to calculate the viscosity average molecular weight of the hyaluronic acid used for creating the calibration curve, hyaluronic acid is dissolved in a 0.2 M sodium chloride solution, a flow time at 30° C. is measured using a Uberode viscometer to calculate a limiting viscosity from the reduced viscosity obtained, whereby the viscosity average molecular weight is calculated using Laurent's equation $[\eta]=0.00036 \times M^{0.78}$ ($[\eta]$: limiting viscosity, M: viscosity average molecular weight).

The equilibrium swelling capacity of the self-crosslinking hyaluronic acid particles is represented by the volume of the self-crosslinking hyaluronic acid particles that is obtained when the aqueous solvent (buffer) of the crosslinked hyaluronic acid composition is removed by filtration and the capacity that is obtained when the self-crosslinking hyaluronic acid particles are further dried.

The equilibrium swelling capacity can be calculated from the following Formula (2), by using a ratio (Qw) between a wet weight of the self-crosslinking hyaluronic acid particles that is obtained when the aqueous solvent (buffer) of the crosslinked hyaluronic acid composition is removed by filtration and a weight of the self-crosslinking hyaluronic acid particles that is obtained when the particles are further dried, and the density.

$$\text{Equilibrium swelling capacity} = 1 + (\rho/\rho_0) \times (Qw - 1) \quad (2)$$

($\rho$: density of self-crosslinking hyaluronic acid particles, $\rho_0$: density of aqueous solvent (buffer))

The equilibrium swelling capacity is influenced by the salt concentration of the solvent, pH, temperature, swelling time, and the like. However, in the invention, it is possible to use a 10 mM phosphate-buffered physiological saline (pH 6.0) having a NaCl concentration of 0.9 wt %, and to measure the equilibrium swelling capacity after the particles are caused to swell for 1 day at 5° C. and reach an equilibrium swelling state.

The method of removing the solvent of the crosslinked hyaluronic acid composition by filtration is not particularly limited, and for example, centrifugal filtration using a centrifugal filter unit, filtration under reduced pressure using a membrane filter, and the like can be used appropriately.

The equilibrium swelling capacity of the self-crosslinking hyaluronic acid particles of the invention is 3-fold to 10-fold and preferably 4-fold to 8-fold. If the equilibrium swelling capacity of the self-crosslinking hyaluronic acid particles is within the above range, a problem that the particles contained in the crosslinked hyaluronic acid composition swell too much and cannot be discharged from a syringe is not caused, and high concentration hyaluronic acid can be injected into the body.

In the crosslinked hyaluronic acid composition of the invention, a dry weight of the self-crosslinking hyaluronic acid particles based on the total volume of the crosslinked hyaluronic acid composition is 3 w/v % to 8 w/v %. For example, the value "3 w/v %" indicates the concentration of the self-crosslinking hyaluronic acid particles in the crosslinked hyaluronic acid composition, and means that when the 1 ml of the crosslinked hyaluronic acid composition is dried under conditions of −20° C., 200 mTorr or less, and 20 hours or longer, the self-crosslinking hyaluronic acid particles are obtained in an amount of 30 mg as a dry weight. The dry weight of the self-crosslinking hyaluronic acid particles based on the total volume of the crosslinked hyaluronic acid composition is preferably 3 w/v % to 7 w/v %.

The concentration of the self-crosslinking hyaluronic acid particles can be quantitated in the following manner, for example. First, a crosslinked hyaluronic acid suspension is diluted with distilled water, a sodium hydroxide solution is added thereto, and the resultant is allowed to standstill at room temperature. In this manner, the ester crosslinks of the self-crosslinking hyaluronic acid are hydrolyzed, and the self-crosslinking hyaluronic acid dissolves. Subsequently, hydrochloric acid is added to the solution for neutralization, and then the concentration of glucuronic acid is quantitated by a carbazole sulfate method. By using the concentration of glucuronic acid and hyaluronic acid, of which the concentration has already been known, as a standard substance, the concentration of the self-crosslinking hyaluronic acid particles can be calculated.

Regarding the crosslinked hyaluronic acid composition of the invention, if the self-crosslinking hyaluronic acid particles are dipped in a 10 mM phosphate-buffered physiological saline at pH 7.0±0.5 and a temperature of 36.0±2.0° C., self-crosslinking hyaluronic acid dissolves completely within 30 days, and hyaluronic acid having a viscosity average molecular weight of 800,000 or more is generated. As typical conditions for generating such hyaluronic acid, the particles are dipped in a 10 mM phosphate-buffered physiological saline at pH 7.4 and a temperature of 37.0° C.

The aqueous solvent contained in the crosslinked hyaluronic acid composition is a solvent which is contained in the crosslinked hyaluronic acid composition such that a dry weight of self-crosslinking hyaluronic acid particles based on the total volume of the crosslinked hyaluronic acid composition becomes 3 w/v % to 8 w/v %. As the aqueous solvent, an aqueous solution having a physiologically acceptable aqueous medium may be preferable. The words "physiologically acceptable" mean that when an agent for treating joints is injected into the joint cavity, the aqueous medium itself does not bring undesirable effects or side effects, for example, swelling, contraction, and inflammation of tissues. Generally, the physiologically acceptable aqueous medium is an aqueous solution of one or more kinds of low-molecular weight substances selected from inorganic salts such as chlorides, sulfates, phosphates, or bicarbonates of alkali or alkaline earth metals, for example, sodium chloride, sodium sulfate, magnesium chloride; salts of organic acids corresponding to the above, such as potassium, calcium salts, sodium lactate, and sodium acetate; and organic neutral substances such as glucose, mannose, and polyol, for example, glycerin and mannitol.

It is possible to prepare the formulation by pharmaceutically known methods according to the form of the formulation, by means of appropriately mixing hyaluronic acid and the like with additives for drugs, such as an appropriate excipient; an isotonizing agent; a preservative; an emulsifier; a dispersant; a stabilizer; a solublizing agent; an antioxidant such as ascorbic acid; a polypeptide (for example, polyarginine or tripeptide) having a low molecular weight (having about less than 10 residues); a protein (for example, serum albumin, gelatin, or immunoglobulin); a hydrophilic polymer (for example, polyvinyl pyrrolidone); an amino acid (for example, glycine, glutamic acid, aspartic acid, or arginine); a chelating agent (for example, EDTA); a counterion (for example, sodium); and/or a nonionic surfactant (for example, polysorbate or poloxamer). Such substances enhancing isotonicity and chemical stability are atoxic to a recipient, in the dose and concentration of the formulation used.

As an index for indicating the storage stability of the crosslinked hyaluronic acid composition according to the invention, the number of days taken for reaching a gel fraction can be used. The number of days taken for reaching a gel fraction refers to the number of days taken for the gel fraction is decreased to a standard value due to slow release of hyaluronic acid when the crosslinked hyaluronic acid composition is allowed to standstill under a certain condition. For example, an aqueous solvent is added to the self-crosslinking hyaluronic acid so as to adjust the concentration thereof to a certain value, and the thus obtained crosslinked hyaluronic acid suspension is heated in a certain environment. At this time, a time taken for the suspension to reach a predetermined gel fraction (for example, a gel fraction of 97% or a gel fraction of 95%) can be determined as the number of days taken for reaching a gel fraction.

The equilibrium sedimentation concentration is the concentration of hyaluronic acid contained in a precipitate that is obtained when the crosslinked hyaluronic acid suspension is allowed to standstill so as to cause the self-crosslinking hyaluronic acid particles to be completely precipitated. In an equilibrium state where an external force is not applied to the crosslinked hyaluronic acid suspension, the equilibrium sedimentation concentration is regarded as an upper limit of the hyaluronic acid concentration. That is, a crosslinked hyaluronic acid suspension in which the hyaluronic acid concentration is the same as the equilibrium sedimentation concentration means that the entire suspension is precipitated without supernatant, and the hyaluronic acid concentration cannot be increased any more.

The equilibrium sedimentation concentration can be obtained from the following Formula (3), by measuring a hyaluronic acid concentration [C], a volume [$V_0$], and a precipitate volume [V] of the suspension-like crosslinked hyaluronic acid composition.

$$\text{Equilibrium sedimentation concentration} = C \times (V_0/V) \qquad (3)$$

The viscosity of the crosslinked hyaluronic acid composition is preferably 300 mPa·s or less at 25±2° C. and a shearing speed of 50 $S^{-1}$. If the viscosity of the crosslinked hyaluronic acid composition is 300 mPa·s or less, the composition can be easily injected as an injection into the body when a syringe is used for injection, and the load on a patient is reduced.

The viscosity of the crosslinked hyaluronic acid composition can be measured using, for example, rotational viscometry. The rotational viscometry can be performed at a shearing speed of 50 $S^{-1}$ and 25° C. by using a con and plate of 1.009° (D=49.938 mm).

When the crosslinked hyaluronic acid composition is injected at a temperature of 25° C. and an injection rate of 50 mm/min by using a syringe having an internal diameter of 0.45 cm to which a 23 G injection needle having an internal diameter of 0.40 mm and a needle length of 25 mm is attached, the discharge pressure of the composition is preferably 0.8 N or less, more preferably 0.2 N to 0.8 N, and even more preferably 0.2 N to 0.6 N. When the crosslinked hyaluronic acid composition having the discharge pressure within the above range is injected as an injection into the body by using a syringe, the composition can be easily injected, and the load on a patient is reduced.

The discharge pressure of the crosslinked hyaluronic acid composition can be measured in a manner in which the crosslinked hyaluronic acid composition is filled in a syringe, an injection needle is attached to the syringe, and the discharge pressure which is applied when the composition is pushed out of the syringe at a predetermined rate is measured by a push-out pressure measuring device. As the push-out pressure measuring device, a device for static compression test can be used for general material tests.

The injection of the invention contains the above crosslinked hyaluronic acid composition. Having a low viscosity and discharge pressure, the injection using the crosslinked hyaluronic acid composition can be easily injected into the body.

It is preferable that the injection of the invention be used such that the self-crosslinking hyaluronic acid is administered at 1.25 mg/kg body weight or a higher dose per administration or in an amount of 75 mg or more per administration. The hyaluronic acid formulation for joints used in the related art has a hyaluronic acid concentration of about 1 w/v % and administered at a dose of about 25 mg per administration. However, since the injection according to the invention uses the crosslinked hyaluronic acid composition that contains the self-crosslinking hyaluronic acid particles having the above predetermined physical properties, the hyaluronic acid concentration can be set to 3 w/v % or higher. Therefore, the injection can be used such that the self-crosslinking hyaluronic acid is administered in an amount of 75 mg or more per administration. Moreover, provided that the average body weight of human beings is regarded as 60 kg, the injection can be used such that the self-crosslinking hyaluronic acid is administered at 1.25 mg/kg body weight or a higher dose per administration.

Preferably, the injection is used such that the self-crosslinking hyaluronic acid is administered at 1.7 mg/kg body weight or a higher dose per administration or in an amount of 100 mg or more per administration. More preferably, the injection is used such that the self-crosslinking hyaluronic acid is administered at 2.0 mg/kg body weight or a higher dose per administration or in an amount of 120 mg or more per administration. In addition, regarding the upper limit, the injection is used such that the self-crosslinking hyaluronic acid is administered at 4.2 mg/kg body weight or a lower dose per administration or in an amount of 250 mg or less per administration. More preferably, the injection is used such that the self-crosslinking hyaluronic acid is administered at 3.3 mg/kg body weight or a lower dose per administration or in an amount of 200 mg or less per administration.

The prefilled syringe formulation of the invention contains the injection inside the syringe barrel, and the injection that uses the crosslinked hyaluronic acid composition as described above has a low viscosity and discharge pressure. Accordingly, the self-crosslinking hyaluronic acid having a high molecular weight can be easily injected into the body.

The crosslinked hyaluronic acid composition of the invention can be administered into the body through any appropriate route of administration. It is preferable that the composition be given by parenteral administration and prepared as an injection. When the crosslinked hyaluronic acid composition according to the invention is administered as an injection into the joint of a rabbit, it is confirmed that the hyaluronic acid having a viscosity average molecular weight of 800,000 or more is generated in the body of the rabbit. It is considered that the crosslinking point of the self-crosslinking hyaluronic acid according to the invention is cut due to the pH or temperature in the body, whereby hyaluronic acid is generated in the joint.

When the crosslinked hyaluronic acid composition of the invention is given by parenteral administration, intramuscular or subcutaneous administration can be performed. Particularly preferably, the composition can be administered directly into a tissue such as joint cavity.

The prescription and the technique for administration are disclosed in, for example, the newest edition and the newest appendix of Japanese Pharmacopoeia, and the final edition of "REMINGTON'S PHARMACEUTICAL SCIENCES" (Maack Publishing Co., Easton, Pa.).

The crosslinked hyaluronic acid composition of the invention can be made into a drug that contains hyaluronic acid in such an amount that is effective for achieving the intended purpose. A "therapeutically effective amount" or a "pharmaceutically effective amount" refers to an amount of a drug that is sufficiently confirmed by a person skilled in the art and effective for producing a pharmaceutical result. How to determine the therapeutically effective amount is sufficiently known to a person skilled in the art.

The "therapeutically effective amount" refers to the amount of a drug that alleviates the state of a disease upon administration. The curative effective and toxicity can be determined by a standard pharmaceutical procedure performed in cell culture or experimental animals. The dose is preferably within the range of a circulating level including LD50 that practically does not have toxicity or does not have toxicity at all. The dose varies within the above range, depending on the form of administration used, susceptibility of a patient, and route of administration. For example, the dose of a complex is selected appropriately according to the age and other conditions of a patient, the type of disease, the type of complex used, and the like.

The self-crosslinking hyaluronic acid particles and the crosslinked hyaluronic acid composition of the invention can also be used in fields other than the knee osteoarthritis without particular limitation, as long as general biodegradable biomedical materials and hyaluronic acid are used in those fields. For example, the self-crosslinking hyaluronic acid particles and the crosslinked hyaluronic acid composition can be used for biomedical products or pharmaceutical compositions, such as carriers of pharmacologically active materials, wound dressing agents, tissue-replacing type biological tissue repairing agents, adhesion-preventing agents, hemostatics, extracelluar matrix of artificial cells, and medical appliances and instruments used for diagnosis and treatment.

EXAMPLES

Hereinafter, the invention will be described based on examples, but the invention is not limited thereto.

Example 1

First Embodiment

<Synthesis of Self-Crosslinking Hyaluronic Acid>

75 g of 2 N nitric acid was put in a rotary and revolutionary kneading device (manufactured by PRIMIX Corporation), followed by cooling at −10° C., thereby obtaining sherbet-like frozen nitric acid. 22.5 g (moisture content of 10%) of sodium hyaluronate powder having a viscosity average molecular weight of 2,200,000 was added to the frozen nitric acid, and the mixture was kneaded and mixed for 1 hour at −10° C. and 100 rpm until it became like uniform rubber (20.8% by mass of sodium hyaluronate).

The mixture of hyaluronic acid and nitric acid was put in a freezer set to −20° C. After 10 days, 1 L of pure water at 5° C. was added thereto, and the pure water was replaced twice at hourly intervals. In addition, 1 L of 50 mM phosphate buffer at 5° C. was added thereto, and the 50 mM phosphate buffer was replaced five times at hourly intervals to neutralize and wash the mixture until the nitric acid is completely removed, thereby obtaining self-crosslinking hyaluronic acid.

<Granulation of Self-Crosslinking Hyaluronic Acid>

After being neutralized, the self-crosslinking hyaluronic acid obtained as above was allowed to standstill for 30 minutes, the supernatant was removed by decantation, and 50 mM phosphate buffer having a weight of 9 times of the weight of the precipitated self-crosslinking hyaluronic acid was added. Subsequently, the self-crosslinking hyaluronic acid suspension was put in a high-speed rotation device (trade name: Clearmix W Motion, manufactured by M Technique Co., Ltd.). A rotor of the device was rotated in the forward direction at 20,000 rpm, a screen thereof was rotated in the backward direction at 18,000 rpm, and the suspension was atomized for 15 minutes while being cooled to a temperature of lower than 50° C. As the rotor, a rotor having a retreat angle of 0° was used, and a screen in which slits on the screen had a width of 1.0 mm was used.

The particle size of the obtained self-crosslinking hyaluronic acid particles was quantitated using a particle size/shape distribution analyzer PITA-1 (manufactured by SEISHIN ENTERPRISE Co., Ltd.). As pre-treatment, the self-crosslinking hyaluronic acid was stained with methylene blue (concentration of staining solution: 1 w/v %, staining time: 1 minute or longer). As measurement conditions of PITA-1, distilled water was used as a carrier fluid, and the size of 10,000 particles was measured with a 4× objective lens. As a result, the average volume particle size of the obtained self-crosslinking hyaluronic acid particles was 65 μm.

Example 2

Self-crosslinking hyaluronic acid was synthesized and granulated in the same manner as in Example 1, except that the treatment time was set to 30 minutes for the obtained self-crosslinking hyaluronic acid. As a result, the average volume particle size of the obtained self-crosslinking hyaluronic acid particles was 52 μm.

Example 3

Self-crosslinking hyaluronic acid was synthesized and granulated in the same manner as in Example 1, except that the treatment time was set to 120 minutes for the obtained self-crosslinking hyaluronic acid. As a result, the average volume particle size of the obtained self-crosslinking hyaluronic acid particles was 41 μm.

Comparative Example 1

The self-crosslinking hyaluronic acid particles obtained in Example 1 were crushed using a high-pressure crushing device (trade name: Nanomizer, manufactured by NANOMIZER Inc.). A collisional generator of ϕ100 μm was mounted on a crushing section of the device, and while cooling was being performed so as to immediately reduce the temperature of the self-crosslinking hyaluronic acid particles to room temperature or a lower temperature, the particles were treated three times at 200 MPa. The particle size of the self-crosslinking hyaluronic acid particles was measured using a laser diffraction/scattering type particle size distribution analyzer (trade name: SALD-7000, manufactured by Shimadzu Corporation). As measurement conditions, a refractive index of the sample was set to 1.300, and 10 mM phosphate-buffered physiological saline was used as a dispersion medium. As a result, the average volume particle size of the obtained self-crosslinking hyaluronic acid particles was 5 μM, but the yield thereof was extremely low and unpractical.

Comparative Example 2

In addition, the self-crosslinking hyaluronic acid prepared according to the above synthesis method of self-crosslinking hyaluronic acid was neutralized and then allowed to standstill for 30 minutes, the supernatant thereof was removed by decantation, and a 50 mM phosphate buffer having a weight of 9 times of the weight of the precipitated self-crosslinking hyaluronic acid was added. Subsequently, the crosslinked hyaluronic acid suspension was put in a high-speed crushing device (trade name: T. K. Homomix, manufactured by PRI-MIX Corporation), the rotor was rotated at 16,000 rpm, and the suspension was crushed for 60 minutes under cooling to reduce the temperature to be lower than 50° C. The particle size of the self-crosslinking hyaluronic acid particles was quantitated using a particle size/shape distribution analyzer PITA-1 (manufactured by SEISHIN ENTERPRISE Co., Ltd.), but the particle size could not be measured since large particles are mixed in the particles. Therefore, the particles were classified using a sieve having mesh openings of 0.2 mm. As a result, since the particles remained on the sieve in a proportion of 90% or higher based on weight, the average volume particle size was determined to be 200 μm or larger.

<Measurement of Half-Life of Solubility>

For the self-crosslinking hyaluronic acid particles of Examples 1 to 3 and Comparative examples 1 and 2 obtained as above, the half-life of solubility was measured. By using a phosphate buffer at pH 7.4, the particles were heated in an environment of 60° C., and samples were collected every 5 hours. The collected sample was diluted and divided into a supernatant and a precipitate by centrifugation, and the hyaluronic acid concentration of each fraction was measured to calculate the gel fraction. The behavior of the gel fraction with respect to the heating time was read, thereby obtaining the heating time taken for reaching a gel fraction of 50%.

<Viscosity Average Molecular Weight>

A phosphate buffer component was added at a concentration of 10 mM to physiological saline, thereby preparing phosphate-buffered saline at pH 7.4. The self-crosslinking hyaluronic acid particles of Examples 1 to 3 and Comparative examples 1 and 2 were added to 100 ml of the phosphate-buffered physiological saline, and the particles were dipped into the saline for 30 days at 37.0° C. until the self-crosslinking hyaluronic acid dissolved completely.

In order to measure the viscosity average molecular weight of the hyaluronic acid eluted in the phosphate-buffered physiological saline, the supernatant was filtered through a 0.2 μm membrane filter, and then 0.1 ml of the resultant was injected into a GPC device. The viscosity average molecular weight was calculated from the retention time of a peak top of molecular weight distribution by using a differential refractometer as a detector of the GPC device. The GPC device used a column of SB806HQ manufactured by SHOWA DENKO K.K. as a GPC column and RI-71S manufactured by Shodex as a differential refractive index detector, and the measurement was performed at a measurement temperature of 40° C. and a flow rate of 0.3 ml/min by using a 0.2 M aqueous solution of sodium nitrate as a solvent. For calculating the viscosity average molecular weight from the retention time, a calibration curve that was created using the retention time of a peak top of the molecular weight distribution of hyaluronic acid of which the viscosity average molecular weight has already been known. The viscosity average molecular weight of the hyaluronic acid used for creating the calibration curve was calculated in a manner in which the hyaluronic acid was dissolved in a 0.2 M sodium chloride solution, a flow time ($t_0$) of the 0.2 M sodium chloride solution and a flow time (t) at 30° C. of a sample solution were measured using a Uberode viscometer, a limiting viscosity at 0 hour was calculated from a reduced viscosity $\eta_{red}$ obtained from $t_0$ and t, and the viscosity average molecular weight was calculated using Laurent's equation $[\eta]=0.00036 \times M^{0078}$ ([$\eta$]: limiting viscosity, M: viscosity average molecular weight).

The measurement results of Examples 1 to 3 and Comparative examples 1 and 2 are shown in Table 2.

In order to quantitate the concentration of the self-crosslinking hyaluronic acid, 50 mg of the crosslinked hyaluronic acid composition was diluted with 1.55 ml of distilled water, and 0.2 ml of a 1 N sodium hydroxide solution was added thereto. The solution was allowed to standstill for 30 minutes at room temperature to cause hydrolysis of ester crosslinks of the self-crosslinking hyaluronic acid, thereby dissolving the self-crosslinking hyaluronic acid. 0.2 ml of 1 N hydrochloric acid was further added thereto for neutralization, and then the concentration of the self-crosslinking hyaluronic acid was calculated by a carbazole sulfate method by using hyaluronic acid (viscosity average molecular weight 1,900,000) of which the concentration had already been known, as a standard substance. Based on the quantitated result, the concentration of the self-crosslinking hyaluronic acid particles was adjusted to 6 w/v %, thereby obtaining a crosslinked hyaluronic acid composition.

Example 5

A crosslinked hyaluronic acid composition was prepared in the same manner as in Example 4, except that self-

TABLE 2

| | Average volume particle size (μm) | | Physical properties | | | | | |
|---|---|---|---|---|---|---|---|---|
| | | | Half-life (hr) | | | Primary molecular weight (ten thousand) | | |
| | Before treatment | After treatment | Before treatment | After treatment | Retention rate (%) | Before treatment | After treatment | Retention rate (%) |
| Example 1 | 500 to 1000 | 65 | 25 | 25 | 100 | 170 | 170 | 100 |
| Example 2 | | 52 | 25 | 24 | 96 | 170 | 170 | 100 |
| Example 3 | | 41 | 25 | 25 | 100 | 170 | 170 | 100 |
| Comparative example 1 | | 5 | 26 | 18 | 69 | 170 | 130 | 76 |
| Comparative example 2 | | 200 or larger | 26 | 26 | 100 | 170 | 170 | 100 |

In the self-crosslinking hyaluronic acid particles of Example 1, the half-life of solubility after treatment was 25 hours, the viscosity average molecular weight was 1,700,000, the retention rate from before treatment was 100%, and the deterioration of physical properties resulting from granulation was not observed. Moreover, the self-crosslinking hyaluronic acid particles of Examples 2 and 3 practically did not exhibit the deterioration of physical properties resulting from granulation. On the other hand, in the self-crosslinking hyaluronic acid particles of Comparative example 1, the half-life of solubility after granulation was 18 hours, the viscosity average molecular weight was 1,300,000, the retention rates from before granulation were 69% and 76%, the deterioration of physical properties resulting from granulation was caused, and the yield was extremely low and unpractical.

Preparation of Crosslinked Hyaluronic Acid Composition

Example 4

The self-crosslinking hyaluronic acid particles obtained in Example 1 were put in 10 mM phosphate-buffered physiological saline at 5° C. and pH 7.0, and the 10 mM phosphate-buffered physiological saline was replaced twice at hourly intervals. The resultant was adjusted as follows such that a dry weight (concentration) of the self-crosslinking hyaluronic acid particles based on the total volume of the crosslinked hyaluronic acid composition became 6 w/v %.

crosslinking hyaluronic acid particles were put in 10 mM phosphate-buffered physiological saline at pH 7.0 such that a dry weight of the self-crosslinking hyaluronic acid particles based on the total volume of the crosslinked hyaluronic acid composition was adjusted to 3 w/v %.

Comparative Example 3

Self-crosslinking hyaluronic acid particles having an average volume particle size of 300 μm were prepared in the same manner as in Example 1, except that a high-speed rotation device (trade name: Clearmix W Motion, manufactured by M Technique Co., Ltd.) was used for granulation of self-crosslinking hyaluronic acid, and a rotor of the device was rotated in a forward direction at 10,000 rpm to perform atomization for 6 minutes under cooling to reduce the temperature of crosslinked hyaluronic acid to be lower than 30° C. Moreover, in the same manner as in Example 4, a crosslinked hyaluronic acid composition in which the concentration of self-crosslinking hyaluronic acid particles was 6 w/v % was prepared.

Comparative Example 4

Self-crosslinking hyaluronic acid particles having an average volume particle size of 153 μm were prepared in the same manner as in Example 1, except that a high-speed rotation device (trade name: Clearmix W Motion, manufactured by M Technique Co., Ltd.) was used for granulation of self-crosslinking hyaluronic acid, and a rotor of the device was rotated in a forward direction at 20,000 rpm to perform atomization for 4 minutes under cooling to reduce the temperature of crosslinked hyaluronic acid to be lower than 30° C. Moreover, in the same manner as in Example 4, a crosslinked hyaluronic acid composition in which the concentration of self-crosslinking hyaluronic acid particles was 6 w/v % was prepared.

Comparative Example 5

Self-crosslinking hyaluronic acid particles having an average volume particle size of 100 μm were prepared in a manner as in which a high-speed rotation device (trade name: Clearmix W Motion, manufactured by M Technique Co., Ltd.) was used for granulation of self-crosslinking hyaluronic acid, and a rotor of the device was rotated in a forward direction at 20,000 rpm to perform atomization for 20 minutes without cooling the self-crosslinking hyaluronic acid. At this time, the temperature of the self-crosslinking hyaluronic acid was raised up to 85° C. Moreover, in the same manner as in Example 4, a crosslinked hyaluronic acid composition in which the concentration of self-crosslinking hyaluronic acid particles was 6 w/v % was prepared.

Reference Example 1

A hyaluronic acid formulation for joints "Suvenyl" (trade name, manufactured by Chugai Pharmaceutical Co., Ltd.) (viscosity average molecular weight 2,000,000, hyaluronic acid concentration 1 w/v %)

Reference Example 2

A hyaluronic acid formulation for joints "Artz" (trade name, manufactured by SEIKAGAKU CORPORATION) (viscosity average molecular weight 800,000, hyaluronic acid concentration 1 w/v %)

Reference Example 3

A hyaluronic acid formulation for joints "Synvisc" (trade name, manufactured by Genzyme Corporation) (hyaluronic acid concentration 0.8 w/v %)

Reference Example 4

A hyaluronic acid formulation for joints "Durolane" (trade name, manufactured by Q-MED) (hyaluronic acid concentration 2.0 w/v %)

Reference Example 5

Physiological saline "Otsuka Normal Saline" (trade name, manufactured by Otsuka Pharmaceutical factory, Inc.)

The properties of the crosslinked hyaluronic acid compositions obtained in Examples 4 and 5 and Comparative examples 3 to 5 were measured and evaluated as follows together with Reference examples 1 to 5.

<Measurement of Viscosity of Crosslinked Hyaluronic Acid Composition>

As a rheometer which is a viscosity measuring device, MCR300 (trade name, manufactured by Physica) was used. By using a cone and plate having a cone angle of 1.009° (D=49.938 mm), the viscosity was measured at 25° C. and a shearing speed of 50 $S^{-1}$. The crosslinked hyaluronic acid compositions of Examples 4 and 5 and Comparative example 3 were compared with Reference examples 1 to 5 in terms of viscosity. The measurement results are shown in Table 3.

TABLE 3

|  | Viscosity (mPa · s) |
| --- | --- |
| Example 4 | 250 |
| Example 5 | 170 |
| Comparative example 3 | 450 |
| Reference example 1 | 1,640 |
| Reference example 2 | 650 |
| Reference example 3 | 1,540 |
| Reference example 4 | 3,390 |
| Reference example 5 | 1 |

As shown in Table 3, particularly, the crosslinked hyaluronic acid composition of Example 4 contained self-crosslinking hyaluronic acid particles at a high concentration such as 6 w/v %, but the viscosity thereof was ⅙ or less of the viscosity of Reference example 1 which had a viscosity average molecular weight of 800,000 and contained hyaluronic acid at 1 w/v %.

<Measurement of Discharge Pressure of Crosslinked Hyaluronic Acid Composition (1)>

1 ml of the crosslinked hyaluronic acid composition was filled in a syringe Terumo syringe SS-01T (trade name, manufactured by TERUMO CORPORATION) having an internal diameter of 0.45 cm, and a 23 G injection needle (manufactured by TERUMO CORPORATION) having an internal diameter of 0.40 mm and a needle length of 25 mm was attached to the syringe. By using a push-out pressure measuring machine EZ-TEST (trade name, manufactured by Shimadzu Corporation), a pressure applied to the syringe of the crosslinked hyaluronic acid compositions of Example 4, Comparative examples 3 and 4, and Reference examples 1 to 5 was measured under discharge conditions of a temperature of 25° C. and a discharge rate of 50 mm/min. The measurement results are shown in Table 4.

TABLE 4

|  | Discharge pressure (N) |
| --- | --- |
| Example 4 | 0.30 |
| Comparative example 3 | Unmeasurable |
| Comparative example 4 | (difficulty in quantitation due to needle clogging) |
| Reference example 1 | 1.20 |
| Reference example 2 | 1.10 |
| Reference example 3 | 1.10 |
| Reference example 4 | 4.00 |
| Reference example 5 | 0.20 |

As shown in Table 4, particularly, the crosslinked hyaluronic acid composition of Example 4 contained hyaluronic acid at a high concentration such as 6 w/v % which was 6 times the concentration in Reference example 1, but the discharge pressure thereof could be kept low.

<Measurement of Discharge Pressure of Crosslinked Hyaluronic Acid Composition (2)>

Injection needles of 24 G, 25 and 27 G which were finer than the 23 G injection needle (internal diameter 0.40 mm) used in Measurement of discharge pressure (1) were used, and 1 ml of samples of Example 4 and Reference examples 1 to 5 were filled in syringes (manufactured by TERUMO CORPORATION) to which the injection needles were attached, whereby a pressure applied to the syringes was measured in the same manner as in Measurement of discharge pressure (1). The results are shown in Table 5 and FIG. 2.

TABLE 5

| Injection needle | | | Discharge pressure (N) | | | | | |
|---|---|---|---|---|---|---|---|---|
| Gage (G) | Internal diameter (mm) | Use | Example 4 | Reference example 1 | Reference example 2 | Reference example 3 | Reference example 4 | Reference example 5 |
| 23 | 0.40 | Intra-arterial/intravenous | 0.3 | 1.2 | 1.1 | 1.1 | 4.0 | 0.2 |
| 24 | 0.37 | Subcutaneous | 0.3 | 1.3 | 1.2 | 1.3 | 4.2 | 0.2 |
| 25 | 0.32 | Subcutaneous | 0.4 | 1.6 | 1.5 | 1.4 | 5.2 | 0.3 |
| 27 | 0.23 | Subcutanaeous/intradermal | 0.8 | 3.0 | 2.7 | Needle clogging | Needle clogging | 0.3 |

Figure 2:
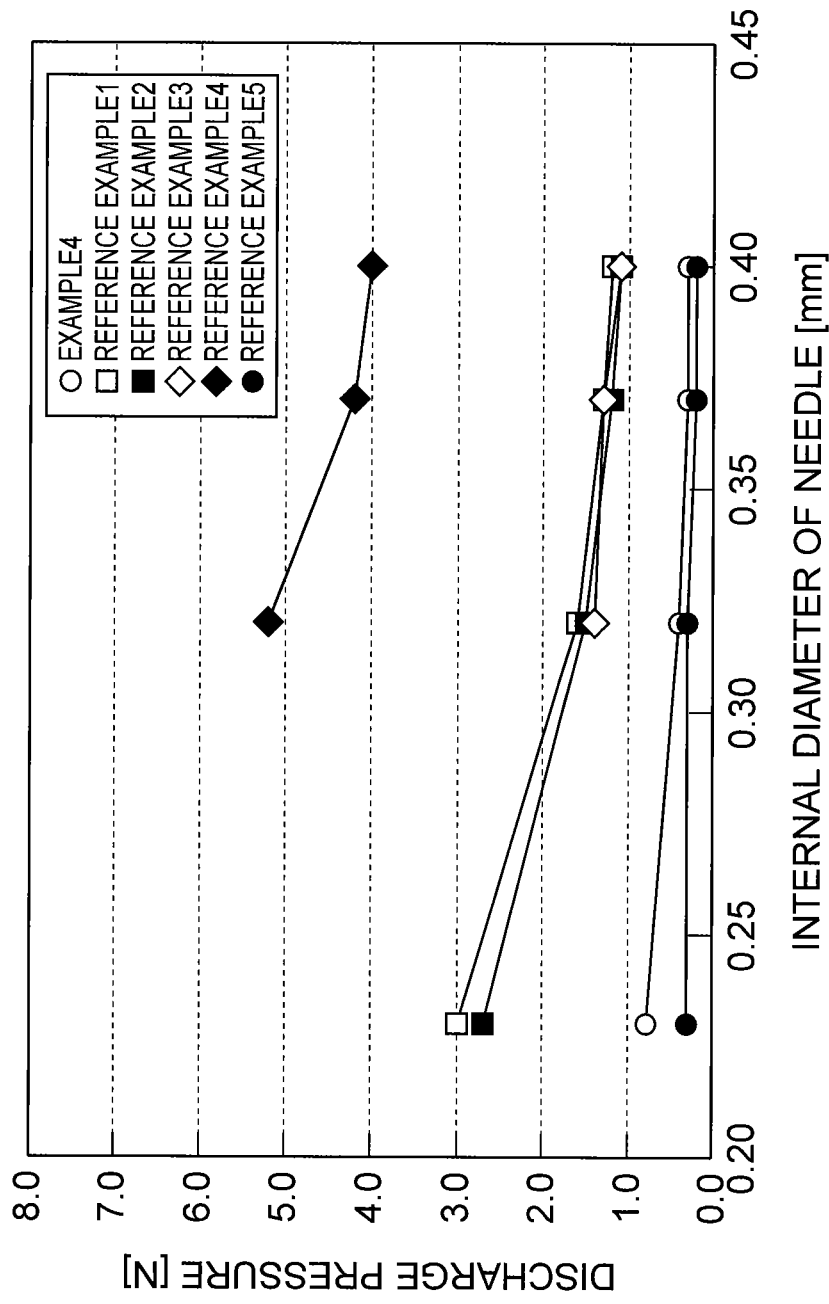
FIG. 2 is a graph showing the comparison between a crosslinked hyaluronic acid composition according to a first embodiment of the invention and hyaluronic acid formulations as reference examples, in terms of a discharge pressure thereof from an injection needle-attached syringe.

As shown in Table 5 and FIG. 2, particularly, the crosslinked hyaluronic acid composition of Example 4 contained hyaluronic acid at a high concentration such as 6 w/v % which is 6 times the concentration in Reference Example 1. However, the discharge pressure thereof could be kept low, and a fine needle could be used for the composition. This implied that the pain of a patient can be reduced at the time of injection.

<Measurement of Primary Molecular Weight of Crosslinked Hyaluronic Acid>

10 mg, which was expressed in terms of self-crosslinking hyaluronic acid, of the samples of Examples 4 and 5 and Comparative example 5 was added to 1 ml of 0.1 N sodium hydroxide solution, and the resultant was allowed to standstill for 30 minutes at 0° C. to dissolve the self-crosslinking hyaluronic acid. 1 ml of 0.1 N hydrochloric acid was added to the solution for neutralization, and the solution was diluted with a GPC solvent to adjust the concentration thereof to 0.01% by mass. The resultant was filtered through a 0.2 µm membrane filter, 0.1 ml of the resultant was injected into the GPC device to measure the viscosity average molecular weight as the primary molecular weight.

The viscosity average molecular weight of the hyaluronic acid was calculated from the retention time of a peak top of molecular weight distribution by using a differential refractometer as a detector of the GPC device. The GPC device used a column of SB806HQ manufactured by SHOWA DENKO K.K. as a GPC column and RI-71S manufactured by Shodex as a differential refractive index detector, and the measurement was performed at a measurement temperature of 40° C. and a flow rate of 0.3 ml/min by using a 0.2 M aqueous solution of sodium nitrate as a solvent. For calculating the viscosity average molecular weight from the retention time, a calibration curve that was created using the retention time of a peak top of the molecular weight distribution of hyaluronic acid of which the viscosity average molecular weight has already been known. The viscosity average molecular weight of the hyaluronic acid used for creating the calibration curve was calculated in a manner in which the hyaluronic acid was dissolved in a 0.2 M sodium chloride solution, a flow time ($t_0$) of the 0.2 M sodium chloride solution and a flow time (t) of a sample solution at 30° C. were measured using a Uberode viscometer, a limiting viscosity at 0 hour was calculated from a reduced viscosity $\eta_{red}$ obtained from $t_0$ and t, and the viscosity average molecular weight was calculated using Laurent's equation $[\eta]=0.00036 \times M^{0.78}$ ($[\eta]$: limiting viscosity, M: viscosity average molecular weight).

<Measurement of Viscosity Average Molecular Weight of Hyaluronic Acid Eluted from Crosslinked Hyaluronic Acid>

A phosphate buffer component was added to physiological saline at a concentration of 10 mM to prepare phosphate-buffered physiological saline at pH 7.4. 0.5 ml of samples of Examples 4 and 5 and Comparative example 5 were added to 100 ml of the phosphate-buffered physiological saline, and dipped in the saline at 37.0° C. for 30 days until the crosslinked hyaluronic acid dissolved completely. The viscosity average molecular weight of the hyaluronic acid eluted in the phosphate-buffered physiological saline was measured in the same manner as in the above-described measurement of viscosity average molecular weight of the crosslinked hyaluronic acid.

TABLE 6

| | Crushing condition | | Primary molecular weight of self-crosslinking hyaluronic acid (ten thousand) | Viscosity average molecular weight of hyaluronic acid eluted from self-crosslinking hyaluronic acid after 30 days (ten thousand) |
|---|---|---|---|---|
| | Temperature control | Temperature (° C.) | | |
| Example 4 | Cooling | <50 | 170 | 170 |
| Example 5 | | | 170 | 170 |
| Comparative example 5 | No cooling | 85 | 70 | 70 |

As shown in Table 6, in Comparative example 5 in which the cooling temperature was not controlled, the primary molecular weight of the self-crosslinking hyaluronic acid decreased during crushing, and the viscosity average molecular weight of the hyaluronic acid eluted from the self-crosslinking hyaluronic acid was decreased to 700,000. On the other hand, in Examples 4 and 5 in which the cooling temperature was controlled to be lower than 50° C. during crushing, the viscosity average molecular weight of the hyaluronic acid eluted from the self-crosslinking hyaluronic acid could be kept high such as 1,700,000.

<Measurement of Viscosity Average Molecular Weight of Hyaluronic Acid Eluted from Self-Crosslinking Hyaluronic Acid in Joints>

Rabbits (Japanese male white rabbits) weighing about 3 kg were anesthetized (anesthetic composition: ketamine (4 ml)+ xylazine (3 ml)+physiological saline (5 ml)), and the samples of Examples 4 and 5, Comparative examples 3 and 5, and Reference examples 1 and 3 were injected at a dose of 0.1 ml/kg into the both knees of their hindlimbs, by using a 23 G injection needle of a syringe having an internal diameter of 0.45 cm.

7 days after the injection, the animals were euthanized under anesthesia. Their knees were excised, and the joint fluid was collected with a pipette for high viscosity. The joint fluid was diluted accurately 100-fold with distilled water and subjected to centrifugation for 10 minutes at 4° C. and 15,000 rpm. The supernatant thereof was filtered through a 0.2 µm membrane filter, and then 0.1 ml of the resultant was injected into a GPC device to measure the viscosity average molecular weight. The measurement results are shown in Table 7.

TABLE 7

|  | Amount of joint fluid (μl) | Viscosity average molecular weight of joint fluid | Hyaluronic acid concentration of joint fluid (% by mass) |
|---|---|---|---|
| Joint fluid to which sample of Example 4 was administered | 300 | 1,700,000 or more | 0.6 |
| Joint fluid to which sample of Example 5 was administered | 200 | 1,700,000 or more | 0.6 |
| Sample of Comparative example 3 | | Unmeasurable (difficulty in injection due to needle clogging) | |
| Joint fluid to which sample of Comparative example 5 was administered | 30 | 1,700,000 or more | 0.3 |
| Joint fluid to which sample of Reference example 1 was administered | 30 | 1,700,000 or more | 0.3 |
| Joint fluid to which sample of Reference example 3 was administered | 30 | 1,700,000 or more | 0.3 |
| Joint fluid to which sample was not administered | 30 | 1,700,000 or more | 0.3 |

As shown in Table 7, in Comparative example 5 and Reference examples 1 and 3, the amount of the joint fluid was 30 μl, the viscosity average molecular weight of the joint fluid was 1,700,000 or more, and the hyaluronic acid concentration was 0.3% by mass, similarly to the joint fluid to which a sample was not administered. On the other hand, in Examples 4 and 5, the amount of the joint fluid was 200 μl and 300 μl, the viscosity average molecular weight of the joint fluid was 1,700,000 or more, and the hyaluronic acid concentration was 0.6% by mass. In addition, injecting Comparative example 3 into the joint was difficult since needle was clogged. The increase in the amount of the joint fluid and the increase in the hyaluronic acid concentration in the joint fluid in Examples 4 and 5 were considered to result from the crosslinked hyaluronic acid composition of the invention. Therefore, it was understood that if the crosslinked hyaluronic acid composition of the invention is used as an injection, the hyaluronic acid having a viscosity average molecular weight of 1,700,000 or more is retained in the joint fluid even 7 days after the injection.

<Measurement of Pain Suppression Effect of Self-Crosslinking Hyaluronic Acid>

By using experimental osteoarthritis induced by subtotal menisectomy performed on the knees of rabbits, the effect of injection of Examples 4 and 5 and Reference examples 1 and 5 into the joint cavity on pain was measured.

<Used Animal and Breeding Method>

As animals, 13-week-old Kbl:JW (SPF) rabbits (male) were prepared in a number of 32 in total such that 8 rabbits were used for each of the examples and reference examples. For 3 to 8 days after the animals were prepared, in order to habituate them to the evaluation device, the animals were put every day in a main container (holder) of an analgesic potency evaluation device for small animals, Incapacitance Tester (manufactured by Linton Instrument), and caused to stop there for 5 seconds.

The animals were individually accommodated in a bracket-type metal wire net floor cage (350 W×500 D×350 H mm) mounted on a movable rack, and bred in an environment of a temperature of 20±3° C., a humidity of 50±20%, number of times of ventilation of 12 to 18 times/hr, and lighting hours of 8:00 to 20:00 (12 hours of light, and 12 hours of darkness).

As feed, solid feed RC 4 for experimental animals (manufactured by Oriental Yeast Co., ltd.) was fed from stainless steel feeder under controlled feeding at 150 g/day. As drinking water, tap water was freely supplied from a polypropylene water-feed bottle (manufactured by Senkan Stainless). In order to identify the individual animal, an individual ID number was marked in the auricle of the animal with a magic marker. Before grouping, a card in which the sex and individual ID number were filled was attached to the cage, and after grouping, a card in which the test number, administration group, sex, animal number, date of operation, date of administration, date of autopsy, and individual ID number were filled was attached to the cage.

<Selection and Grouping of Animals>

Grouping was performed the day before the date of subtotal menisectomy. On the day of grouping, the weight and weight distribution in both the hindlimbs of all animals were measured. From the measured weight distribution in both the hindlimbs, a proportion of the weight distributed to the left hindlimb ((load on left/total load on both hindlimbs)×100 (%)) was calculated. Based on the proportion of the weight distributed to the left hindlimb, the animals were selected in order from an individual showing the value close to the average. The selected animals were allocated into each group by using stratified continuous random sampling based on the proportion of the weight distribution in distributed to the left hindlimb. It was confirmed that the average of the proportion of the weight distributed to the left hindlimb was the same in the respective groups, and there was no difference in the value between the groups. Thereafter, it was confirmed that the average of the weight was the same in the respective groups, and there was no difference in the value between the groups.

<Preparation of Osteoarthritis Model (Subtotal Menisectomy)>

The subtotal menisectomy was performed the day after grouping, and the date of the subtotal menisectomy was defined as postoperative day 0. By using 14- to 15-week-old animals, osteoarthritis model having undergone subtotal menisectomy were prepared with reference to the methods disclosed in Reference documents 1 to 3.

Herein, among the above reference documents, for example, Reference document 1 discloses the following procedure. 32 KBL:JW domestic rabbits (13-week-old, female) are prepared, the lateral collateral ligament and sesamoid ligament of their left knee joint are excised under anesthesia with ketamine and xylazine, and the meniscus is partially excised by 3.0 mm to 4.0 mm. By using a 26 G injection needle, a high-molecular weight HA solution is injected 5 times per 2 weeks into the knee joint of 8 animals in each of groups A and B, physiological saline is injected into 8 animals of a control group C, Loxonin is orally administered every day to the groups C and D, and the pain suppression effect and cartilage degeneration preventing effect are evaluated. In addition, Reference document 2 discloses the following procedure. 72 New Zealand white domestic rabbits (weighing 2 kg to 3 kg) are prepared, the ligament of their left knee joint is excised under anesthesia, and the meniscus is partially excised by 3 mm to 4 mm. a 1% to 0.01% HA solution having a molecular weight of 1,900,000 is injected twice a week for 2 and 4 weeks into the knee joint of 48 rabbits of group A, a 1% to 0.01% HA solution having a molecular weight of 800,000 is injected to 12 rabbits of group B, and physiological saline is injected into 12 rabbits of group C. After the animals are sacrificed, their knee joints are collected to evaluate the drug efficacy. Moreover, Reference document 3 discloses the following procedure. The lateral collateral ligament and sesamoid ligament of the left knee joint of 15

Japanese white domestic rabbits (female, 2.5 kg) are excised under anesthesia with sodium pentobarbital, and the meniscus is partially excised by 3.0 mm to 4.0 mm. By using a 25 G injection needle, a HA solution is injected twice a week into the knee joint, and as a control, physiological saline is injected in the same amount. After the animals are sacrificed, their knee joints are collected to evaluate the drug efficacy.

Reference document 1: M. Mihara, S. Higo, Y. Uchiyama, K. Tanabe, K. Saito: Different effects of high molecular weight sodium hyaluronate and NSAID on the progression of the cartilage degeneration in rabbit OA model, Osteoarthritis and Cartilage, Vol. 15, No. 5, pp. 543-549 (2007)

Reference document 2: T. Kikuchi, H. Yamada and M. Shimmei: Effect of high molecular weight hyaluronan on cartilage degeneration in a rabbit model of osteoarthritis, Osteoarthritis and Cartilage, Vol. 4, No. 2, pp. 99-110 (1996)

Reference document 3: Toshiyuki Kikuchi, Haruki Yamada, Takumi Horita, Tomoaki Tateda, Nobuichi Komatsu, and Masayuki Shimmei: Cartilage degeneration inhibition effect of high molecular weight hyaluronan in domestic rabbit model of osteoarthritis, Joint surgery, Vol. 15, No. 11, 92-98 (1996)

Reference document 4: Tomoaki Tateda, Haruhiro Eihou, Katsuharu Iwatate, and Tom Nakamura: Test for drug efficacy and pharmacology of a sodium hyaluronate formulation (ME3710) in a rabbit model of experimental osteoarthritis (OA) and fixed joint contracture (PS), Pharmacology and Treatment, 23, 833-841 (1995)

Reference document 5: Yumi Nochi, Naomi Hachiki, Yasuhiro Ota, Katsuharu Iwatate, Koichi Tamoto, and Akira Sekigawa: Bioquivalance test for a novel high-molecular weight sodium hyaluronate formulation that can be stored at room temperature, Pharmacology and treatment, 33, 303-312 (2005)

Reference document 6: Koji Watanabe, Osamu Namiki, Hiromichi Toshima, and Takeo Kusumoto: Effect of high-molecular weight hyaluronic acid on fixed joints, Basic science for orthopedics, Vol. 9, 77-79 (1982)

Reference document 7: Kyosuke Miyazaki, Kiyoshi Nagano, Keitaro Suzuki, Sachiko Goto, Toshijiro Yamaguchi, and Osamu Namiki: Effect of sodium hyaluronate on fixed joint of rabbit, Basic science for orthopedics, Vol. 11, 125-127 (1984)

Reference document 8: T. kawano, H. Miura, T. Mawatari, T. Moro-Oka, Y. Nakanishi, H Higashi and Y. Iwamoto: Mechanical Effects of the Intraarticular Administration of High Molecular Weight Hyaluronic Acid Plus Phospholipid on Synovial Joint Lubrication and Prevention of Articular Cartilage Degeneration in Experimental Osteoarthritis, Arthritis & Rheumatism, Vol. 48, No. 7, pp. 1923-1929 (2003)

Specifically, under the anesthesia concurrently using ketamine hydrochloride (trade name: Ketalar 500 mg for intramuscular injection, manufactured by Sankyo Yell Pharmaceutical Co., Ltd.) and xylazine (trade name: Skillpe, 2% injection, manufactured by Intervet K.K.) (intramuscular injection in the femoral region), hair in the left knee joint region of the rabbit was removed, and the rabbit was fixed to a Kitajima fixing device (manufactured by NATSUME SEISAKUSHO CO., LTD.) in a supine position. An incision of about 2 cm was made in the skin just below the outside of the patella under an aseptic condition, so as to expose the lateral collateral ligament, and then the ligament was excised. In addition, the tendon of the origin of popliteus muscle was excised to expose the lateral meniscus, and the periphery of the region positioned in approximately the center of the meniscus was excised by 3.0 mm to 4.0 mm. Thereafter, interrupted suture is made in the subcutaneous layer and the skin respectively, and about 0.2 ml of ampicillin (trade name: Viccillin sol 15%, manufactured by Meiji Seki Pharma Co., Ltd.) was injected into the muscle of the femoral region.

<Constitution of Group for Injection into Joint Cavity>

Four groups in which the injections of Examples 4 and 5 and Reference examples 1 and 5 were injected at 0.1 mL/kg into the joint cavity were set as shown in Table 8, with reference to the methods disclosed in Reference documents 1 to 8.

TABLE 8

| Group | Date of administration | Dose (mL/kg) | Date of autopsy | Number of animals |
|---|---|---|---|---|
| Example 4 | Postoperative day 4 | 0.1 | Postoperative day 21 | 8 |
| Example 5 | Postoperative day 4 | 0.1 | Postoperative day 21 | 8 |
| Reference example 1 | Postoperative day 4 | 0.1 | Postoperative day 21 | 8 |
| Reference example 5 | Postoperative day 4 | 0.1 | Postoperative day 21 | 8 |

For all animals in all groups, after the weight distribution in both hindlimbs was measured on postoperative day 4 (date of onset of pain), the injections of Examples 4 and 5 and Reference examples 1 and 5 were administered once at 0.1 ml/kg into the cavity of the (left) knee joint having undergone operation, by using a 1 ml syringe barrel (Terumo syringe 1 ml for tuberculin, TERUMO CORPORATION) and a 23 G injection needle (Terumo injection needle 23 G, TERUMO CORPORATION). The dose of the injection administered was individually calculated by being converted into the amount of the injection based on the weight measured on the date of administration.

<Method of Measuring Pain Suppression Effect>

For measuring the weight distribution in both hindlimbs, Incapacitance Tester (manufactured by Linton Instrument UK) as an analgesic potency evaluation device for small animals was used. This device accurately detects the weight distributed to the left and right legs of the animal put in the main container, by using a dual-channel sensor pad disposed at the bottom of the container, by means of measuring the weight of each of the left and right legs in grams. The thus obtained values were averaged based on the time set by a tester. As the main container, a container for rabbit was used, and the time set for measurement was set to 5 seconds in a state where the animal stopped.

The animal was transferred into the main container (holder) for rabbit, and the measurement was performed in a state where the animal stopped (first measurement). Thereafter, the animal was taken out of the holder and then put in the holder again, and the measurement was performed in a state where the animal stopped (second measurement). This operation was repeated again (third measurement). Regarding the weight distribution in both hindlimbs measured three times, a proportion of the weight distributed to the left hindlimb (%) was calculated from the weight (load) on left and right hindlimbs by the following Formula (4).

$$\text{Proportion of weight distributed to left hindlimb (\%)} = \{\text{load on left }(g)/(\text{load on right }(g)+\text{load on left }(g))\times 100\} \quad (4)$$

An average of the proportion of the weight distributed to the left hindlimb (%) that was calculated three times was defined as a proportion of the weight distributed to the left hindlimb (%) per measurement. The results are shown in FIG. 3.

Figure 3:
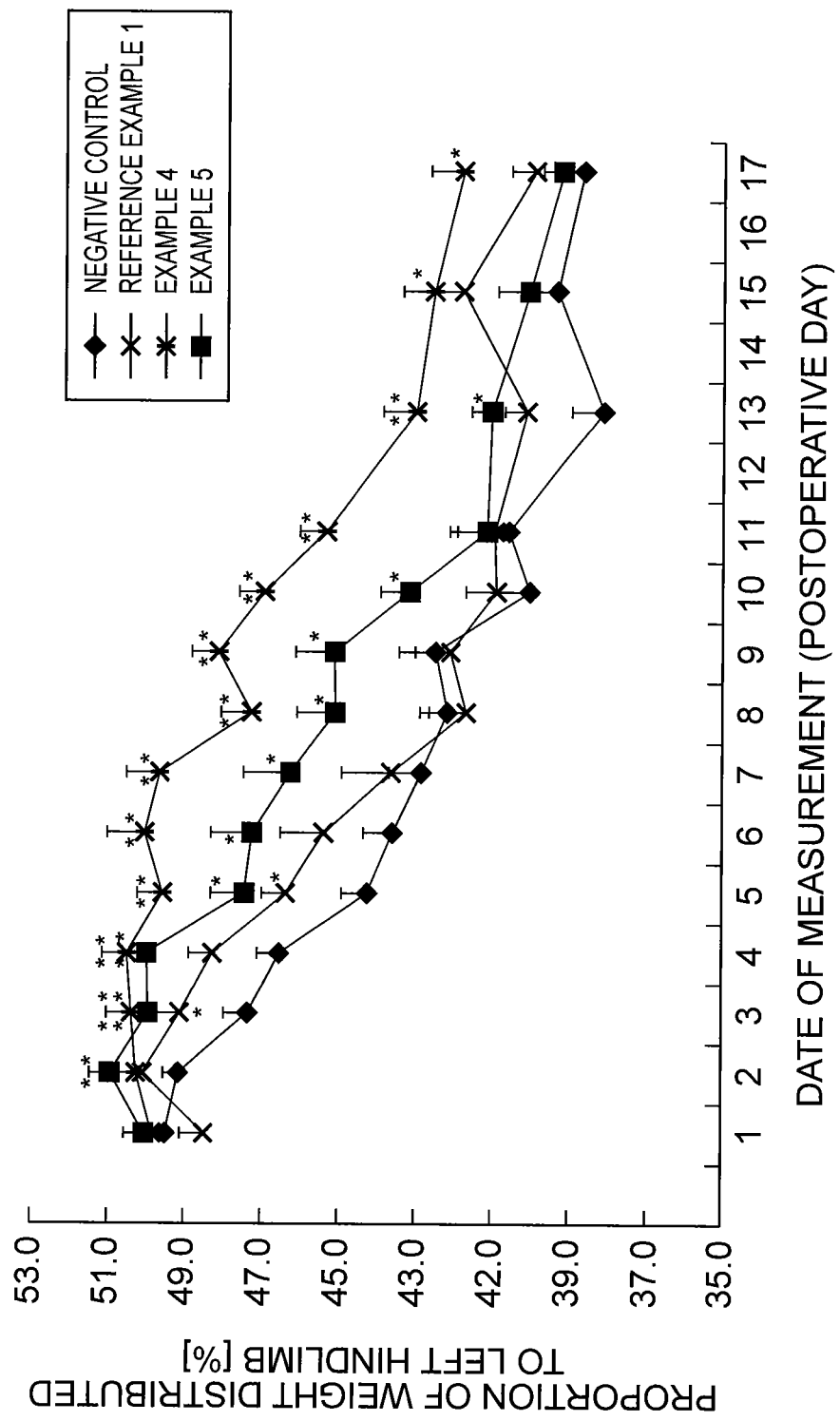
FIG. 3 is a graph showing the comparison between the crosslinked hyaluronic acid composition according to the first embodiment of the invention and hyaluronic acid formulations as reference examples, in terms of a pain suppression effect.
Figure 4:
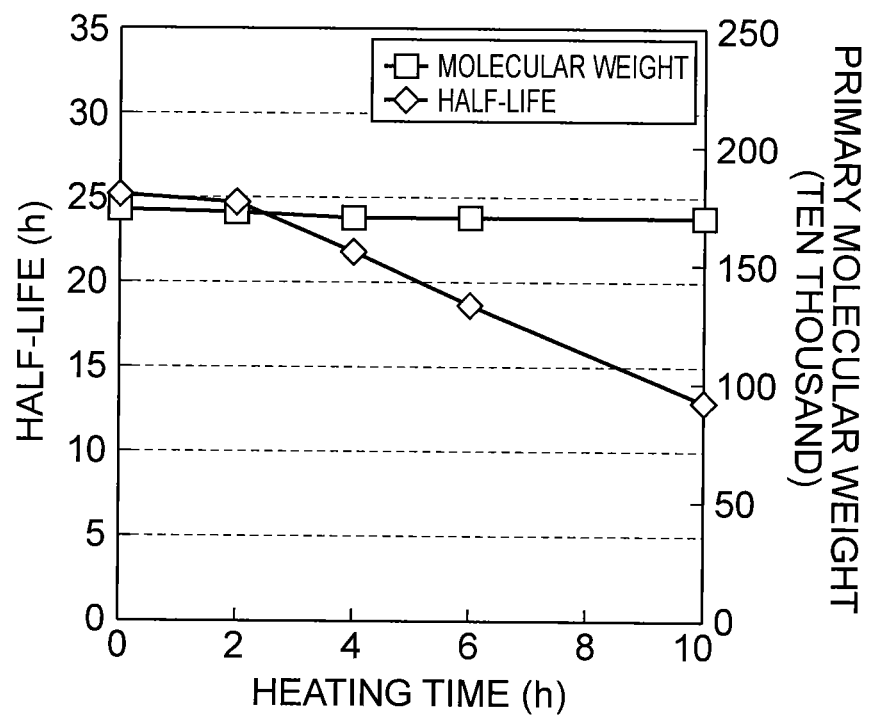
FIG. 4 is a graph showing the change in a half-life and a primary molecular weight over heating time of self-crosslinking hyaluronic acid particles according to the first embodiment.
Figure 5:
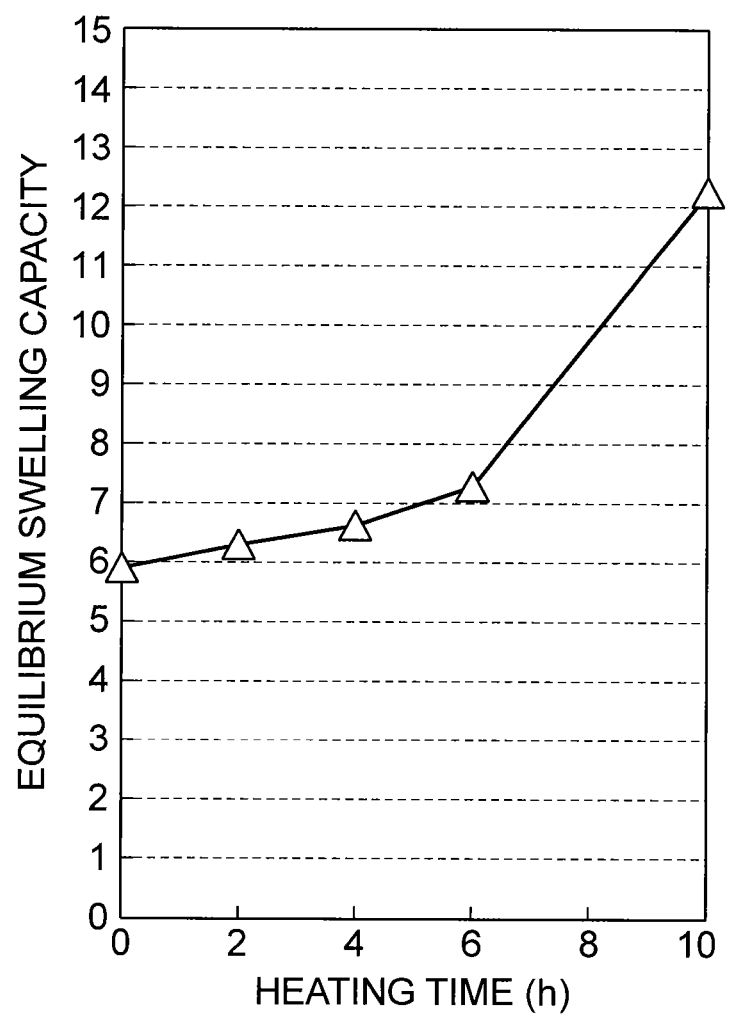
FIG. 5 is a graph showing the change in an equilibrium swelling capacity over heating time of the self-crosslinking hyaluronic acid particles according to the first embodiment.
Figure 6:
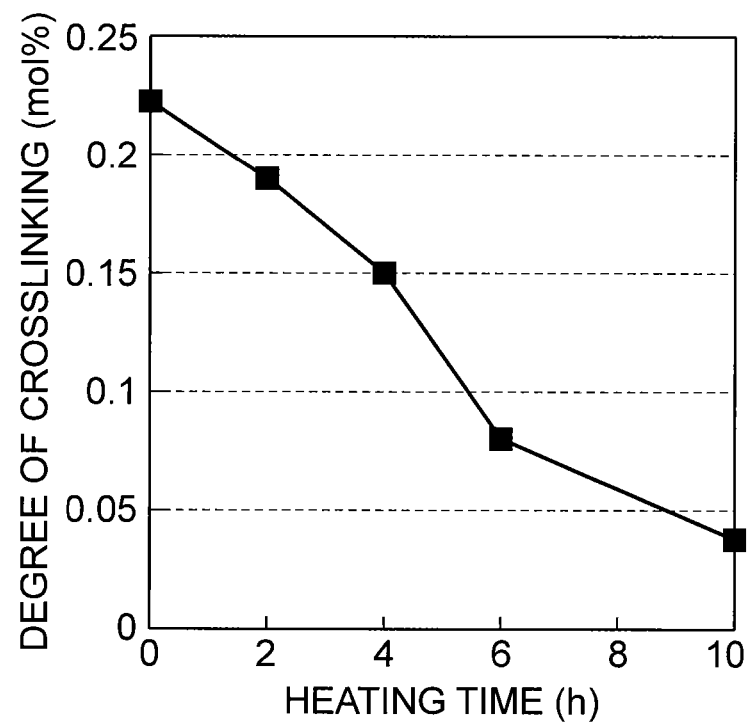
FIG. 6 is a graph showing the change in a degree of crosslinking over heating time of the self-crosslinking hyaluronic acid particles according to the first embodiment.
Figure 7:
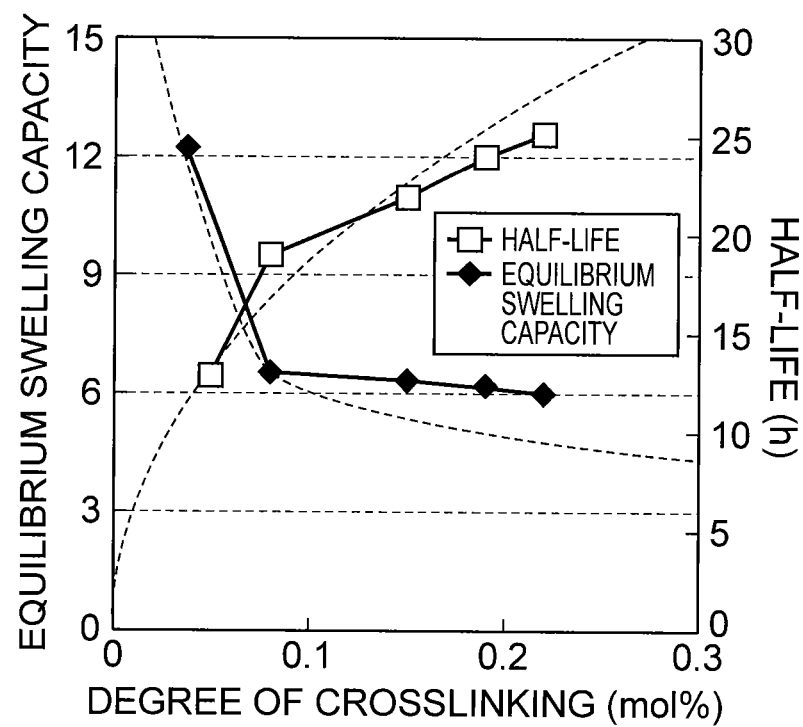
FIG. 7 is a graph showing the change in an equilibrium swelling capacity and a half-life with a degree of crosslinking of the self-crosslinking hyaluronic acid particles according to the first embodiment.

As shown in FIG. 3, it was understood that the self-crosslinking hyaluronic acid of Examples 4 and 5 exhibits the improvement in the pain suppression effect compared to Reference example 1. In addition, in FIG. 3, * and ** mean that there is a significant difference between a group and a negative control (group administered with physiological saline) as Reference example 5 (*: $p<0.05$, **: $p<0.01$ (t-test)).

<Preparation of Self-Crosslinking Hyaluronic Acid Having Various Types of Degree of Self-Crosslinking Esterification>

The solvent of the self-crosslinking hyaluronic acid obtained in Example 1 was replaced with 50 mM phosphate-buffered physiological saline (pH 7.4), thereby preparing 6 wt % of a suspension-like crosslinked hyaluronic acid composition. 7 ml of the obtained crosslinked hyaluronic acid composition was collected and transferred to a container and sealed. The crosslinked hyaluronic acid composition was repeatedly collected in the same manner, thereby obtaining 5 test samples.

The 5 test samples were put in a testing machine of a constant temperature environment (manufactured by ESPEC CORP) set to 60° C. and heated for a preset time. The five test samples were heated for different heating time. That is, at each point time when 0, 2, 4, 6, and 10 hours elapsed after the beginning of heating, the test samples were taken out one by one. By the above process, five types of crosslinked hyaluronic acid compositions were obtained. These were named Examples 6 to 9 and Comparative example 6, in the ascending order of the heating time.

<Measurement of Equilibrium Swelling Capacity>

0.4 ml of the crosslinked hyaluronic acid composition was subjected to centrifugation for 30 minutes at 5° C. and 2,000 rpm by using a centrifugal filter unit (a pore diameter of 0.45 µm, manufactured by Millipore Corporation), thereby removing the solvent. Moreover, each centrifugal filter unit was dried for 20 hours to obtain the weight of the self-crosslinking hyaluronic acid from which the solvent had been removed and the weight of the dried self-crosslinking hyaluronic acid, thereby calculating the equilibrium swelling capacity. 10 mM phosphate-buffered physiological saline (pH 6.0) was used as a solvent, and the NaCl concentration was 0.9 wt %. After the composition reached the equilibrium swelling state by being caused to swell for 1 day at 5° C., the equilibrium swelling capacity was measured.

<Measurement of Half-Life of Solubility at 60° C.>

The crosslinked hyaluronic acid compositions of Examples 6 to 9 and Comparative example 6 were measured in terms of the half-life of solubility at 60° C., in the same manner as the measurement methods in Examples 1 to 3 and Comparative example 1 and 2.

<Measurement of Primary Molecular Weight>

As the primary molecular weight of the crosslinked hyaluronic acid compositions of Examples 6 to 9 and Comparative example 6, the viscosity average molecular weight was measured in the same manner as the measurement method in Examples 1 to 3 and Comparative examples 1 and 2.

<Measurement of Degree of Crosslinking (Degree of Self-Crosslinking Esterification)>

The degree of crosslinking (degree of self-crosslinking esterification) in the self-crosslinking hyaluronic acid was obtained from the intensity of chemical shift (the value of a peak area) by proton nuclear magnetic resonance (NMR). For the measurement, it is necessary to lower the molecular weight of hyaluronic acid by hydrolyzing the hyaluronic acid structure in advance. Accordingly, hydrolysis was performed using a hyaluronic acid hydrolase for selectively hydrolyzing only the main chain structure of the self-crosslinking hyaluronic acid. As the hyaluronic acid hydrolase, Hyaluronidaze from sheep testes Type V, lyophilized powder, activity: >1,500 units/mg solid (manufactured by Sigma-Aldrich Co.) was used. In order to remove impurities, purification was performed using a cation exchange column Mono S 5/50 GL (manufactured by GE Healthcare). During the purification, the above enzyme was dissolved in a 10 mM acetate buffer at pH 5.0 so as to yield a concentration of 0.1 g/mL, and 0.1 mL of this solution was passed through the above column that was brought to equilibrium by the same buffer, thereby obtaining 0.8 mL of an enzyme solution as a purified fraction that was eluted at a NaCl concentration of 0.05 mol/L to 0.15 mol/L. During the hydrolysis treatment, the crosslinked hyaluronic acid was adjusted such that the concentration thereof in 1.0 mL of 10 mM acetate-buffered physiological saline at pH 5.0 became 3 wt %, 0.2 mL of the above purified enzyme solution was added thereto, the resultant was reacted for 24 hours under a shaking condition at 37° C. and 160 rpm, and then 0.2 mL of the enzyme solution was added thereto, followed by reaction for 24 hours under the same condition. The solution having undergone reaction was frozen at −30° C., then subjected to freeze drying for 18 hours, and then used as a measurement sample for NMR.

In addition, the measurement conditions were as follows. Instrument: AVANCEIII 500, observation width: 500.232 MHz, pulse width: 10.5 µs (90°), measurement mode: 13 C decoupling-1H non-decoupling method, number of times of integration: 760 times, measurement temperature: 30° C.

From the spectrum obtained by the measurement, the integral values of the chemical shift ($H_a$: 4.18 ppm) corresponding to the crosslinked ester group and the chemical shift ($H_b$: 2.05 ppm) corresponding to the acetyl methyl group were calculated, and the degree of crosslinking was calculated by the following Formula (5).

$$\text{Degree of crosslinking} = 100 \times ([H_a] \times 2)/([H_b]/3) \quad (5)$$

The measurement results of the crosslinked hyaluronic acid compositions of Examples 6 to 9 and Comparative example 6 are shown in Table 9 and FIGS. 4 to 7.

TABLE 9

| | Heating time (h) | Degree of crosslinking (mol %) | Primary molecular weight (ten thousand) | Half-life of solubility at 60° C. (h) | Equilibrium swelling capacity |
|---|---|---|---|---|---|
| Example 6 | 0 | 0.22 | 170 | 25 | 5.9 |
| Example 7 | 2 | 0.19 | 170 | 24 | 6.2 |
| Example 8 | 4 | 0.15 | 170 | 22 | 6.6 |
| Example 9 | 6 | 0.08 | 170 | 19 | 7.3 |
| Comparative example 6 | 10 | 0.04 | 170 | 13 | 12.3 |

As shown in Table 9 and FIGS. 4 to 7, in the crosslinked hyaluronic acid compositions of which the degree of crosslinking was reduced by increasing the heating time, the half-life of solubility at 60° C. was also shortened, which showed the correlation of a quadratic function. On the other hand, the equilibrium swelling capacity increased as much as that of the crosslinked hyaluronic acid compositions of which the degree of crosslinking was reduced, and this showed the correlation similar to the Flory-Rehner equation.

<Evaluation of Storage Stability>

The solvent of the crosslinked hyaluronic acid compositions of Examples 6 to 9 and Comparative example 6 was replaced with 10 mM phosphate-buffered physiological saline (pH 6.0) so as to adjust the concentration of the self-crosslinking hyaluronic acid to 6 w/v %. Collection of samples was performed at an appropriate interval during heating in an environment at 60° C., and the amount of hyaluronic acid released was measured, thereby measuring the gel fraction. The behavior of the gel fraction with respect to the heating time was read, and the heating time taken for reaching a gel fraction of 97% was obtained. Moreover, the heating time taken for reaching a gel fraction of 95% was also obtained in the same manner as above. The measurement results are shown in the following Table 10 and FIGS. 8 and 9.

TABLE 10

|  | | Value of physical properties | | | Number of days taken for reaching gel fraction | |
| --- | --- | --- | --- | --- | --- | --- |
|  | Heating time (h) | Primary molecular weight (ten thousand) | Half-life of solubility at 60° C. (h) | Degree of crosslinking (mol %) | Based on 97% (day) | Based on 95% (day) |
| Example 6 | 0 | 170 | 25 | 0.22 | 3.9 | 5.0 |
| Example 7 | 2 | 170 | 24 | 0.19 | 2.9 | 4.2 |
| Example 8 | 4 | 170 | 22 | 0.15 | 2.1 | 2.9 |
| Example 9 | 6 | 170 | 19 | 0.08 | 1.3 | 2.3 |
| Comparative example 6 | 10 | 170 | 13 | 0.04 | 0.7 | 1.1 |

Figure 8:
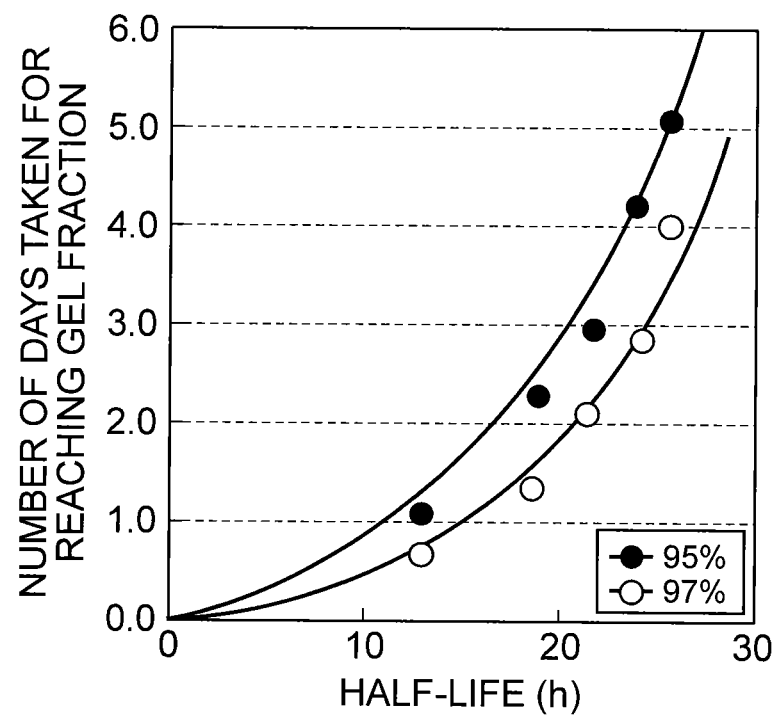
FIG. 8 is a graph showing the change in the number of days taken for reaching a gel fraction with a half-life of the self-crosslinking hyaluronic acid particles according to the first embodiment.
Figure 9:
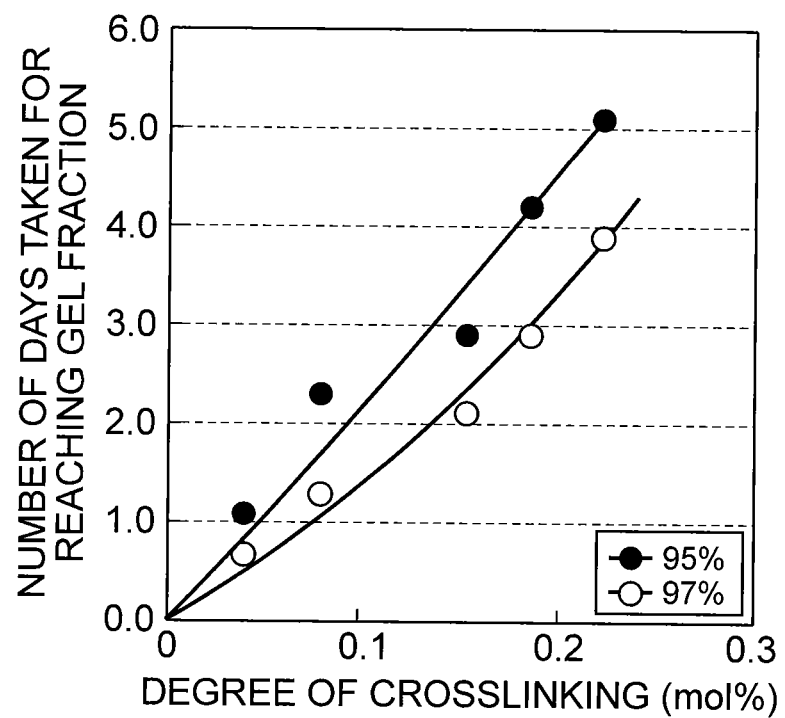
FIG. 9 is a graph showing the change in the number of days taken for reaching a gel fraction with a degree of crosslinking of the self-crosslinking hyaluronic acid particles of the first embodiment.

As shown in Table 10, as the heating time increased, the number of days taken for reaching a gel fraction decreased. Particularly, in Comparative example 6, the heating time taken for reaching a gel fraction of 97% was reduced to 0.7 days, and the heating time taken for reaching a gel fraction of 95% was reduced to 1.1 days. In addition, as the half-life and the degree of crosslinking decreased, the number of days taken for reaching a gel fraction also decreased, and this showed that the value of these physical properties is correlated with the storage stability (FIGS. 8 and 9).

(Measurement of Equilibrium Sedimentation Concentration)

Further, the crosslinked hyaluronic acid suspensions of Examples 6 to 9 and Comparative example 6 were measured in terms of the equilibrium sedimentation concentration. The equilibrium sedimentation concentration was obtained by the following Formula (6), by measuring a hyaluronic acid concentration [C] of the suspension, a volume [$V_0$] of the suspension, and the volume [V] of the precipitate.

$$\text{Equilibrium sedimentation concentration} = C \times (V_0/V) \quad (6)$$

The measurement results are shown in the following Table 11.

TABLE 11

|  | Heating time (h) | Average sedimentation concentration (% by weight) |
| --- | --- | --- |
| Example 6 | 0 | 11.3 |
| Example 7 | 2 | 10.9 |
| Example 8 | 4 | 8.8 |
| Example 9 | 6 | 8.1 |
| Comparative example 6 | 10 | 5.2 |

As shown in Table 11, the equilibrium sedimentation concentration as a settable upper limit of the concentration was correlated with the heating time. Particularly, Comparative example 6 had a low average sedimentation concentration such as 5.2% by weight, and this showed that the concentration thereof cannot be increased to be as high as that of Examples 6 to 9.

Example 10

Second Embodiment

<Pretreatment for Removing Ethanol in Raw Material of Hyaluronic Acid>

Sodium hyaluronate powder having a viscosity average molecular weight of 2,200,000 was put in a ventilation filter-attached container, and the powder was aspirated by a pump at room temperature and aerated for 3 days, thereby removing ethanol.

<Synthesis of Self-Crosslinking Hyaluronic Acid>

75 g of 2 N nitric acid was put in a rotary and revolutionary kneading device (manufactured by PRIMIX Corporation), followed by cooling at −10° C., thereby obtaining sherbet-like frozen nitric acid. 22.5 g (moisture content of 10%) of sodium hyaluronate powder treated as above was added to the frozen nitric acid, and the mixture was kneaded and mixed for 1 hour at −10° C. and 100 rpm until it became like uniform rubber (20.8% by mass of sodium hyaluronate).

The mixture of hyaluronic acid and nitric acid was put in a freezer set to −20° C. After 10 days, 1 L of pure water at 5° C. was added thereto, and the pure water was replaced twice at hourly intervals. In addition, 1 L of 50 mM phosphate buffer at 5° C. was added thereto, and the 50 mM phosphate buffer was replaced five times at hourly intervals to neutralize and wash the mixture until the nitric acid is completely removed, thereby obtaining self-crosslinking hyaluronic acid.

<Granulation of Self-Crosslinking Hyaluronic Acid>

After being neutralized, the self-crosslinking hyaluronic acid obtained as above was allowed to standstill for 30 minutes, the supernatant was removed by decantation, and 50 mM phosphate buffer having a weight of 9 times of the weight of the precipitated self-crosslinking hyaluronic acid was added. Subsequently, the self-crosslinking hyaluronic acid suspension was put in a high-speed rotation device (trade name: Clearmix W Motion, manufactured by M Technique Co., Ltd.). A rotor of the device was rotated in the forward direction at 20,000 rpm, a screen thereof was rotated in the backward direction at 18,000 rpm, and the suspension was atomized for 15 minutes while being cooled to a temperature of less than 50° C. As the rotor, a rotor having a retreat angle of 0° was used, and a screen in which slits on the screen have a width of 1.0 mm was used.

Example 11

Self-crosslinking hyaluronic acid particles were obtained in the same manner as in Example 10, by using a raw material of hyaluronic acid adjusted to contain 1,000 ppm of ethanol.

Comparative Example 7

Self-crosslinking hyaluronic acid particles were obtained in the same manner as in Example 10, by using a raw material of hyaluronic acid adjusted to contain 31,000 ppm of ethanol.

Comparative Example 8

Self-crosslinking hyaluronic acid particles were obtained in the same manner as in Example 10, by using a raw material of hyaluronic acid adjusted to contain 116,000 ppm of ethanol.

<Measurement of Degree of Self-Crosslinking Esterification (Degree of Crosslinking)>

The degree of crosslinking (degree of self-crosslinking esterification) in the self-crosslinking hyaluronic acid was obtained from the intensity of chemical shift (the value of a peak area) by proton nuclear magnetic resonance (NMR). For the measurement, it is necessary to lower the molecular weight of hyaluronic acid by hydrolyzing the hyaluronic acid structure in advance. Accordingly, hydrolysis was performed using a hyaluronic acid hydrolase which selectively hydrolyzes only the main chain structure of the self-crosslinking hyaluronic acid. As the hyaluronic acid hydrolase, Hyaluronidaze from sheep testes Type V, lyophilized powder, activity: >1,500 units/mg solid (manufactured by Sigma-Aldrich Co.) was used. In order to remove impurities, purification was performed using a cation exchange column Mono S 5/50 GL (manufactured by GE Healthcare). During the purification, the above enzyme was dissolved in a 10 mM acetate buffer at pH 5.0 so as to yield a concentration of 0.1 g/mL, and 0.1 mL of this solution was passed through the above column that was brought to equilibrium by the same buffer, thereby obtaining 0.8 mL of an enzyme solution as a purified fraction that was eluted at a NaCl concentration of 0.05 mol/L to 0.15 mol/L. During the hydrolysis, the crosslinked hyaluronic acid was prepared such that the concentration thereof in 1.0 mL of 10 mM acetate-buffered physiological saline at pH 5.0 became 3 wt %, 0.2 mL of the above purified enzyme solution was added thereto, the resultant was reacted for 24 hours under a vibration condition at 37° C. and 160 rpm, and then 0.2 mL of the enzyme solution was added thereto, followed by reaction for 24 hours under the same condition. The solution having undergone reaction was frozen at −30° C., then subjected to freeze drying for 18 hours, and then used as a measurement sample for NMR.

From the spectrum obtained by the measurement, the integral values of the chemical shift ($H_a$: 4.18 ppm) corresponding to the crosslinked ester group and the chemical shift ($H_b$: 2.05 ppm) corresponding to the acetyl methyl group were calculated, and the degree of crosslinking was calculated by the following Formula (4).

$$\text{Degree of crosslinking}=100\times([H_a]\times 2)/([H_b]/3) \quad (4)$$

<Measurement of Amount of Ethyl Ester>

The self-crosslinking hyaluronic acid particles of Examples 10 and 11 and Comparative examples 7 and 8 obtained as above were measured in terms of the amount of ethyl ester by NMR.

From the spectrum obtained by the measurement, the integral values of the peak ($H_a$: 4.27 ppm to 4.33 ppm) corresponding to the ethyl ester group of the hyaluronic acid and the peak ($H_b$: 2.05 ppm) corresponding to the acetyl methyl group of the hyaluronic acid were calculated, and the ethyl ester in the hyaluronic acid was quantitated by the following Formula (5).

Amount of ethyl ester in hyaluronic acid $$(\text{mol \%})=100\times([H_a]\times 2)/([H_b]/3) \quad (5)$$

<Measurement of Half-Life of Solubility>

The self-crosslinking hyaluronic acid particles of Examples 10 and 11 and Comparative examples 7 and 8 obtained as above were measured in therms of the half-life of solubility. By using a phosphate buffer at pH 7.4, the particles were heated in an environment of 60° C., and samples were collected every 5 hours. The collected sample was diluted and divided into a supernatant and a precipitate by centrifugation, and the hyaluronic acid concentration of each fraction was measured to calculate the gel fraction. The behavior of the gel fraction with respect to the heating time was read, thereby obtaining the heating time taken for reaching a gel fraction of 50%.

<Viscosity Average Molecular Weight>

A phosphate buffer component was added to physiological saline at a concentration of 10 mM to prepare phosphate-buffered physiological saline at pH 7.4. The self-crosslinking hyaluronic acid particles of Examples 10 and 11 and Comparative examples 7 and 8 were added to 100 ml of the phosphate-buffered physiological saline, and dipped in the saline at 37.0° C. for 30 days untile the crosslinked hyaluronic acid dissolved completely.

In order to measure the viscosity average molecular weight of the hyaluronic acid eluted in the phosphate-buffered physiological saline, the supernatant was filtered through a 0.2 μm membrane filter, and then 0.1 ml of the hyaluronic acid was injected into a GPC device. The viscosity average molecular weight of the hyaluronic acid was calculated from the retention time of peak tops of molecular weight distribution by using a differential refractometer as a detector of the GPC device. The GPC device used a column of SB806HQ manufactured by SHOWA DENKO K.K. as a GPC column and RI-71S manufactured by Shodex as a differential refractive index detector, and the measurement was performed at a measurement temperature of 40° C. and a flow rate of 0.3 ml/min by using a 0.2 M aqueous solution of sodium nitrate as a solvent. For calculating the viscosity average molecular weight from the retention time, a calibration curve that was created using the retention time of a peak top of the molecular weight distribution of hyaluronic acid of which the viscosity average molecular weight has already been known. The viscosity average molecular weight of the hyaluronic acid used for creating the calibration curve was calculated in a manner in which the hyaluronic acid was dissolved in a 0.2 M sodium chloride solution, a flow time ($t_0$) of the 0.2 M sodium chloride solution and a flow time (t) at 30° C. of a sample solution were measured using a Uberode viscometer, a limiting viscosity at 0 hour was calculated from a reduced viscosity $\eta_{red}$ obtained from $t_0$ and t, and the viscosity average molecular weight was calculated using Laurent's equation $[\eta]=0.00036\times M^{0.78}$ ($[\eta]$: limiting viscosity, M: viscosity average molecular weight).

The measurement results of Examples 10 and 11 and Comparative examples 7 and 8 are shown in Table 12.

TABLE 12

| | Content of ethanol (ppm) | Amount of ethyl ester (mol %) | Degree of self-crosslinking esterification (mol %) | Half-life of solubility (h) | Primary molecular weight (ten thousand) |
|---|---|---|---|---|---|
| Example 10 | 20 or less | 0 | 0.22 | 25 | 170 |
| Example 11 | 1,000 | 0.03 | 0.22 | 25 | 170 |
| Comparative example 7 | 31,000 | 0.84 | 0.14 | 20 | 145 |
| Comparative example 8 | 116,000 | 1.89 | 0.09 | 9 | 114 |

As shown in Table 12, in the self-crosslinking hyaluronic acid particles of Examples 10 and 11, the content of ethanol was small, the amount of ethyl ester was also small, and decreased in the half-life of solubility and the primary molecular weight was not observed. On the other hand, in the self-crosslinking hyaluronic acid particles of Comparative examples 7 and 8 having a large content of ethanol and a large amount of ethyl ester, the value of the half-life of solubility and the primary molecular weight was smaller compared to Examples 10 and 11, and the physical properties deteriorated. Moreover, the degree of self-crosslinking esterification of Comparative examples 7 and 8 was lower than that of Examples 10 and 11. Therefore, it was confirmed that ethyl esterification hinders self esterification.

<Average Volume Particle Size>

The particle size of the obtained self-crosslinking hyaluronic acid particles obtained in Example 10 was measured using a particle size/shape distribution analyzer PITA-1 (manufactured by SEISHIN ENTERPRISE Co., Ltd.). As pre-treatment, the self-crosslinking hyaluronic acid was stained with methylene blue (concentration of staining solution: 1 w/v %, staining time: 1 minute or longer). As measurement conditions of PITA-1, distilled water was used as a carrier fluid, and the size of 10,000 particles was measured with a 4× objective lens. As a result, the average volume particle size of the obtained self-crosslinking hyaluronic acid particles was 65 μm.

<Preparation of Crosslinked Hyaluronic Acid Composition>

Example 12

The self-crosslinking hyaluronic acid particles obtained in Example 10 were put in 10 mM phosphate-buffered physiological saline at 5° C. and pH 7.0, and the 10 mM phosphate-buffered physiological saline was replaced twice at hourly intervals. The resultant was adjusted as follows such that the rate of a dry weight (concentration) of the self-crosslinking hyaluronic acid particles to the total volume of the crosslinked hyaluronic acid composition became 6 w/v %.

In order to quantitate the concentration of the self-crosslinking hyaluronic acid, 50 mg of the crosslinked hyaluronic acid composition was diluted with 1.55 ml of distilled water, and 0.2 ml of a 1 N sodium hydroxide solution was added thereto. The solution was allowed to standstill for 30 minutes at room temperature to cause hydrolysis of ester crosslinks of the self-crosslinking hyaluronic acid, thereby dissolving the self-crosslinking hyaluronic acid. 0.2 ml of 1 N hydrochloric acid was further added thereto for neutralization, and then the concentration of the self-crosslinking hyaluronic acid was calculated by a carbazole sulfate method by using hyaluronic acid (viscosity average molecular weight 1,900,000) of which the concentration had already been known as a standard substance. Based on the quantitated result, the concentration of the self-crosslinking hyaluronic acid particles was adjusted to be 6 w/v %, thereby obtaining a crosslinked hyaluronic acid composition.

Example 13

A crosslinked hyaluronic acid composition was prepared in the same manner as in Example 12, except that self-crosslinking hyaluronic acid particles were put in 10 mM phosphate-buffered physiological saline at pH 7.0 such that the rate of a dry weight of the self-crosslinking hyaluronic acid particles to the total volume of the crosslinked hyaluronic acid composition became 3 w/v %.

Comparative Example 9

Self-crosslinking hyaluronic acid particles having an average volume particle size of 300 μm were prepared in the same manner as in Example 10, except that a high-speed rotation device (trade name Clearmix W Motion, manufactured by M Technique Co., Ltd.) was used for granulation of self-crosslinking hyaluronic acid, and a rotor of the device was rotated in a forward direction at 10,000 rpm to perform atomization for 6 minutes under cooling to reduce the temperature of crosslinked hyaluronic acid to be lower than 30° C. Moreover, in the same manner as in Example 12, a crosslinked hyaluronic acid composition in which the concentration of self-crosslinking hyaluronic acid particles was 6 w/v % was prepared.

Comparative Example 10

Self-crosslinking hyaluronic acid particles having an average volume particle size of 153 μm were prepared in the same manner as in Example 10, except that a high-speed rotation device (trade name: Clearmix W Motion, manufactured by M Technique Co., Ltd.) was used for granulation of self-crosslinking hyaluronic acid, and a rotor of the device was rotated in a forward direction at 20,000 rpm to perform atomization for 4 minutes under cooling to reduce the temperature of crosslinked hyaluronic acid to be lower than 30° C. Moreover, in the same manner as in Example 12, a crosslinked hyaluronic acid composition in which the concentration of self-crosslinking hyaluronic acid particles was 6 w/v % was prepared.

Comparative Example 11

Self-crosslinking hyaluronic acid particles having an average volume particle size of 100 μm were prepared in the manner in which a high-speed rotation device (trade name: Clearmix W Motion, manufactured by M Technique Co., Ltd.) was used for granulation of self-crosslinking hyaluronic acid, and a rotor of the device was rotated in a forward direction at 20,000 rpm to perform atomization for 20 minutes without cooling self-crosslinking hyaluronic acid. At this time, the temperature of self-crosslinking hyaluronic acid was raised up to 85° C. Moreover, in the same manner as in Example 12, a crosslinked hyaluronic acid composition in which the concentration of self-crosslinking hyaluronic acid particles was 6 w/v % was prepared.

Reference Example 1

A hyaluronic acid formulation for joints "Suvenyl" (trade name, manufactured by Chugai Pharmaceutical Co., Ltd.) (viscosity average molecular weight 2,000,000, hyaluronic acid concentration 1 w/v %)

Reference Example 2

A hyaluronic acid formulation for joints "Artz" (trade name, manufactured by SEIKAGAKU CORPORATION) (viscosity average molecular weight 800,000, hyaluronic acid concentration 1 w/v %)

Reference Example 3

A hyaluronic acid formulation for joints "Synvisc" (trade name, manufactured by Genzyme Corporation) (hyaluronic acid concentration 0.8 w/v %)

Reference Example 4

A hyaluronic acid formulation for joints "Durolane" (trade name, manufactured by Q-MED) (hyaluronic acid concentration 2.0 w/v %)

Reference Example 5

Physiological saline "Otsuka Normal Saline" (trade name, manufactured by Otsuka Pharmaceutical factory, Inc.)

The properties of the crosslinked hyaluronic acid compositions obtained in Examples 12 and 13 and Comparative examples 9 to 11 were measured and evaluated as follows together with Reference examples 1 to 5.

<Measurement of Viscosity of Crosslinked Hyaluronic Acid Composition>

As a rheometer which is a viscosity measuring instrument, MCR300 (trade name, manufactured by Physica) was used. By using a cone and plate having a cone angle of 1.009° (D=49.938 mm), the viscosity was measured at 25° C. and a shearing speed of 50 $S^{-1}$. The crosslinked hyaluronic acid compositions of Examples 12 and 13 and Comparative example 9 were compared with Reference examples 1 to 5 in terms of the viscosity. The measurement results are shown in Table 13.

TABLE 13

|  | Viscosity (mPa · s) |
| --- | --- |
| Example 12 | 250 |
| Example 13 | 170 |
| Comparative example 9 | 450 |
| Reference example 1 | 1,640 |
| Reference example 2 | 650 |
| Reference example 3 | 1,540 |
| Reference example 4 | 3,390 |
| Reference example 5 | 1 |

As shown in Table 13, particularly, the crosslinked hyaluronic acid composition of Example 12 contained the self-crosslinking hyaluronic acid particles at a high concentration such as 6 w/v %, but the viscosity thereof became ⅙ of that of Reference example 1 having a viscosity average molecular weight of 800,000 and a hyaluronic acid concentration of 1 w/v %.

<Discharge Pressure Measurement of Crosslinked Hyaluronic Acid Composition (1)>

1 ml of the crosslinked hyaluronic acid composition was filled in a syringe Terumo syringe SS-01T (trade name, manufactured by TERUMO CORPORATION) having an internal diameter of 0.45 cm, and a 23 G injection needle (manufactured by TERUMO CORPORATION) having an internal diameter of 0.40 mm and a needle length of 25 mm was attached to the syringe. By using a push-out pressure measuring machine EZ-TEST (trade name, manufactured by Shimadzu Corporation), a pressure applied to the syringe of the crosslinked hyaluronic acid compositions of Example 12, Comparative examples 9 and 10, and Reference examples 1 to 5 was measured under discharge conditions of a temperature of 25° C. and a discharge rate of 50 mm/min. The measurement results are shown in Table 14.

TABLE 14

|  | Discharge pressure (N) |
| --- | --- |
| Example 12 | 0.30 |
| Comparative example 9 | Unmeasurable |
| Comparative example 10 | (difficulty in quantitation due to needle clogging) |
| Reference example 1 | 1.20 |
| Reference example 2 | 1.10 |
| Reference example 3 | 1.10 |
| Reference example 4 | 4.00 |
| Reference example 5 | 0.20 |

As shown in Table 14, particularly, the crosslinked hyaluronic acid composition of Example 12 contained hyaluronic acid at a high concentration such as 6 w/v % which was 6 times the concentration in Reference example 1, but the discharge pressure thereof could be kept low.

<Discharge Pressure Measurement of Crosslinked Hyaluronic Acid Composition (2)>

Injection needles of 24 G, 25 G, and 27 G which were finer than the 23 G injection needle (internal diameter 0.40 mm) used in Discharge pressure measurement (1) were used, and 1 ml of samples of Example 12 and Reference examples 1 to 5 were filled in syringes (manufactured by TERUMO CORPORATION) to which the injection needles were attached, whereby a pressure applied to the syringes was measured in the same manner as in Discharge pressure measurement (1). The results are shown in Table 15 and FIG. 10.

TABLE 15

| | Injection needle | | Discharge pressure (N) | | | | | |
| --- | --- | --- | --- | --- | --- | --- | --- | --- |
| Gage (G) | Internal diameter (mm) | Use | Example 12 | Reference example 1 | Reference example 2 | Reference example 3 | Reference example 4 | Reference example 5 |
| 23 | 0.40 | Intra-arterial/intravenous | 0.3 | 1.2 | 1.1 | 1.1 | 4.0 | 0.2 |
| 24 | 0.37 | Subcutaneous | 0.3 | 1.3 | 1.2 | 1.3 | 4.2 | 0.2 |
| 25 | 0.32 | Subcutaneous | 0.4 | 1.6 | 1.5 | 1.4 | 5.2 | 0.3 |
| 27 | 0.23 | Subcutanaeous/intradermal | 0.8 | 3.0 | 2.7 | Needle clogging | Needle clogging | 0.3 |

Figure 10:
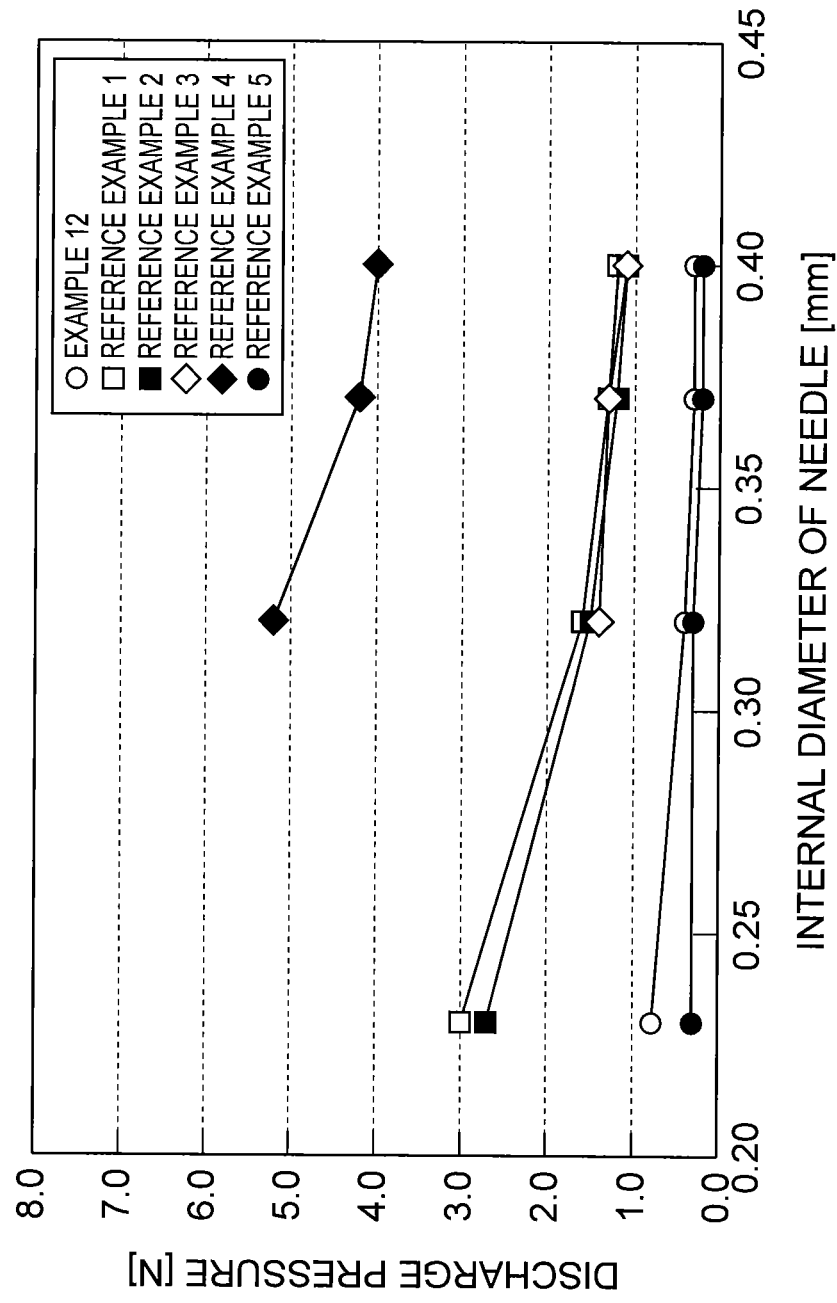
FIG. 10 is a graph showing the comparison between a crosslinked hyaluronic acid composition according to a second embodiment of the invention and hyaluronic acid formulations as reference examples, in terms of a discharge pressure thereof from an injection needle-attached syringe.

As shown in Table 15 and FIG. 10, particularly, the crosslinked hyaluronic acid composition of Example 12 contained hyaluronic acid at a high concentration such as 6 w/v % which is 6 times the concentration in Reference Example 1. However, the discharge pressure thereof could be kept low, and a fine needle can be used for the composition. This implied that the pain of a patient can be reduced at the time of injection.

<Measurement of Primary Molecular Weight of Crosslinked Hyaluronic Acid>

10 mg, which was expressed in terms of self-crosslinking hyaluronic acid, of the samples of Examples 12 and 13 and Comparative example 11 was added to 1 ml of 0.1 N sodium hydroxide solution, and the resultant was allowed to standstill for 30 minutes at 0° C. to dissolve the self-crosslinking hyaluronic acid. 1 ml of 0.1 N hydrochloric acid was added to the solution for neutralization, and the solution was diluted with a GPC solvent to adjust the concentration thereof to 0.01% by mass. After the resultant was filtered through a 0.2 μm membrane filter, 0.1 ml of the resultant was injected into the GPC device to measure the viscosity average molecular weight as the primary molecular weight, in the same manner as in Examples 10 and 11 and Comparative examples 7 and 8. The measurement results are shown in Table 16.

<Measurement of Viscosity Average Molecular Weight of Hyaluronic Acid Eluted from Crosslinked Hyaluronic Acid>

A phosphate buffer component was added to physiological saline at a concentration of 10 mM to prepare phosphate-buffered physiological saline at pH 7.4. 0.5 ml of samples of Examples 12 and 13 and Comparative example 11 were added to 100 ml of the phosphate-buffered physiological saline, and dipped in the saline at 37.0° C. for 30 days until the crosslinked hyaluronic acid dissolved completely. The viscosity average molecular weight of the hyaluronic acid eluted in the phosphate-buffered physiological saline was measured in the same manner as in Examples 10 and 11 and Comparative examples 7 and 8. The measurement results are shown in Table 16

TABLE 16

| | Crushing condition | | Primary molecular weight of self-crosslinking hyaluronic acid (ten thousand) | Viscosity average molecular weight of hyaluronic acid eluted from self-crosslinking hyaluronic acid after 30 days (ten thousand) |
|---|---|---|---|---|
| | Temperature control | Temperature (° C.) | | |
| Example 12 | Cooling | <50 | 170 | 170 |
| Example 13 | | | 170 | 170 |
| Comparative example 11 | No cooling | | 85 | 70 | 70 |

As shown in Table 16, In Comparative example 11 in which cooling temperature was not controlled, the primary molecular weight of the self-crosslinking hyaluronic acid decreased during crushing, and the viscosity average molecular weight of the hyaluronic acid eluted from the self-crosslinking hyaluronic acid was as low as 700,000. On the other hand, in Examples 12 and 13 in which cooling temperature was controlled to be lower than 50° C. during crushing, the viscosity average molecular weight of the hyaluronic acid eluted from the self-crosslinking hyaluronic acid could be kept to be as high as 1,700,000.

<Measurement of Viscosity Average Molecular Weight of Hyaluronic Acid Eluted from Self-Crosslinking Hyaluronic Acid in Joint>

Rabbits (Japanese male white rabbits) weighing about 3 kg were anesthetized (anesthetic composition: ketamine (4 ml)+ xylazine (3 ml)+physiological saline (5 ml)), and the samples of Examples 12 and 13, Comparative examples 9 and 11, and Reference examples 1 and 3 were injected at a dose of 0.1 ml/kg into the both knees of their hindlimbs, by using a 23 G injection needle of a syringe having an internal diameter of 0.45 cm.

7 days after the injection, the animals were euthanized under anesthesia. Their knees were excised, and the joint fluid was collected with a pipette for high viscosity. The joint fluid was diluted accurately 100-fold with distilled water and subjected to centrifugation for 10 minutes at 4° C. and 15,000 rpm. The supernatant thereof was filtered through a 0.2 μm membrane filter, and then 0.1 ml of the resultant was injected into a GPC device to measure the viscosity average molecular weight. The measurement results are shown in Table 17.

TABLE 17

| | Amount of joint fluid (μl) | Viscosity average molecular weight of joint fluid | Hyaluronic acid concentration of joint fluid (% by mass) |
|---|---|---|---|
| Joint fluid to which sample of Example 12 was administered | 300 | 1,700,000 or more | 0.6 |
| Joint fluid to which sample of Example 13 was administered | 200 | 1,700,000 or more | 0.6 |
| Sample of Comparative example 9 | Unmeasurable (difficulty in injection due to needle clogging) | | |
| Joint fluid to which sample of Comparative example 11 was administered | 30 | 1,700,000 or more | 0.3 |
| Joint fluid to which sample of Reference example 1 was administered | 30 | 1,700,000 or more | 0.3 |
| Joint fluid to which sample of Reference example 3 was administered | 30 | 1,700,000 or more | 0.3 |
| Joint fluid to which sample was not administered | 30 | 1,700,000 or more | 0.3 |

As shown in Table 17, in Comparative example 11 and Reference examples 1 and 3, the amount of the joint fluid was 30 μl, the viscosity average molecular weight of the joint fluid was 1,700,000 or more, and the hyaluronic acid concentration was 0.3% by mass or higher, similarly to the case to which a sample was not administered. On the other hand, in Examples 12 and 13, the amount of the joint fluid was 200 μl and 300 μl, and the viscosity average molecular weight of the joint fluid was 1,700,000 or more, and the hyaluronic acid concentration was 0.6% by mass. In addition, injecting Comparative example 9 into the joint was difficult since the needle was clogged. The increase in the amount of the joint fluid and the increase in the hyaluronic acid concentration in the joint fluid in Examples 12 and 13 were considered to result from the crosslinked hyaluronic acid composition of the invention. Therefore, it was understood that if the crosslinked hyaluronic acid composition of the invention is used as an injection, the hyaluronic acid having a viscosity average molecular weight of 1,700,000 or more is retained in the joint fluid even 7 days after the injection.

<Measurement of Pain Suppression Effect of Self-Crosslinking Hyaluronic Acid>

By using experimental osteoarthritis induced by subtotal menisectomy performed on the knees of rabbits, the effect of injection of Examples 12 and 13 and Reference examples 1 and 5 into the joint cavity on pain was measured.

<Used Animal and Breeding Method>

As animals, 13-week-old Kbl:JW (SPF) rabbits (male) were prepared in a number of 32 in total such that 8 rabbits were used for each of the examples and reference examples. For 3 to 8 days after the animals were prepared, in order to habituate them to the evaluation device, the animals were put every day in a main container (holder) of an analgesic potency evaluation device for small animals, Incapacitance Tester (manufactured by Linton Instrument), and caused to stop there for 5 seconds.

The animals were individually accommodated in a bracket-type metal wire net floor cage (350 W×500 D×350 H mm) mounted on a movable rack, and bred in an environment of a temperature of 20±3° C., a humidity of 50±20%, number of times of ventilation of 12 to 18 times/hr, and lighting hours of 8:00 to 20:00 (12 hours of light, and 12 hours of darkness). As feed, solid feed RC 4 for experimental animals (manufactured by Oriental Yeast Co., ltd.) was fed from stainless steel feeder under controlled feeding at 150 g/day. As drinking water, tap water was freely supplied from a polypropylene water-feed bottle (manufactured by Senkan Stainless). In order to identify the individual animal, an individual ID number was marked in the auricle of the animal with a magic marker. Before grouping, a card in which the sex and individual ID number were filled was attached to the cage, and after grouping, a card in which the test number, administration group, sex, animal number, date of operation, date of administration, date of autopsy, and individual ID number were filled was attached to the cage.

<Selection and Grouping of Animals>

Grouping was performed the day before the date of subtotal menisectomy. On the day of grouping, the weight and weight distribution in both the hindlimbs of all animals were measured. From the measured weight distribution in both the hindlimbs, a proportion of the weight distributed to the left hindlimb ((load on left/total load on both hindlimbs)×100 (%)) was calculated. Based on the proportion of the weight distributed to the left hindlimb, the animals were selected in order from an individual showing the value close to the average. The selected animals were allocated into each group by using stratified continuous random sampling based on the proportion of the weight distribution in distributed to the left hindlimb. It was confirmed that the average of the proportion of the weight distributed to the left hindlimb was the same in the respective groups, and there was no difference in the value between the groups. Thereafter, it was confirmed that the average of the weight was the same in the respective groups, and there was no difference in the value between the groups.

<Preparation of Osteoarthritis Model (Subtotal Menisectomy)>

The subtotal menisectomy was performed the day after grouping, and the date of the subtotal menisectomy was defined as postoperative day 0. By using 14- to 15-week-old animals, osteoarthritis model having undergone subtotal menisectomy were prepared with reference to the methods disclosed in Reference documents 1 to 3.

Specifically, under the anesthesia concurrently using ketamine hydrochloride (trade name: Ketalar 500 mg for intramuscular injection, manufactured by Sankyo Yell Pharmaceutical Co., Ltd.) and xylazine (trade name: Skillpe, 2% injection, manufactured by Intervet K.K.) (intramuscular injection in the femoral region), hair in the left knee joint region of the rabbit was removed, and the rabbit was fixed to a Kitajima fixing device (manufactured by NATSUME SEISAKUSHO CO., LTD.) in a supine position. An incision of about 2 cm was made in the skin just below the outside of the patella under an aseptic condition, so as to expose the lateral collateral ligament, and then the ligament was excised. In addition, the tendon of the origin of popliteus muscle was excised to expose the lateral meniscus, and the periphery of the region positioned in approximately the center of the meniscus was excised by 3.0 mm to 4.0 mm. Thereafter, interrupted suture is made in the subcutaneous layer and the skin respectively, and about 0.2 ml of ampicillin (trade name: Viccillin sol 15%, manufactured by Meiji Seki Pharma Co., Ltd.) was injected into the muscle of the femoral region.

<Constitution of Group for Injection into Joint Cavity>

Four groups in which the injections of Examples 12 and 13 and Reference examples 1 and 5 were injected at 0.1 mL/kg into the joint cavity were set as shown in Table 18, with reference to the methods disclosed in Reference documents 1 to 8.

TABLE 18

| Group | Date of administration | Dose (mL/kg) | Date of autopsy | Number of animals |
|---|---|---|---|---|
| Example 12 | Postoperative day 4 | 0.1 | Postoperative day 21 | 8 |
| Example 13 | Postoperative day 4 | 0.1 | Postoperative day 21 | 8 |
| Reference example 1 | Postoperative day 4 | 0.1 | Postoperative day 21 | 8 |
| Reference example 5 | Postoperative day 4 | 0.1 | Postoperative day 21 | 8 |

For all animals in all groups, after the weight distribution in both hindlimbs was measured on postoperative day 4 (date of onset of pain), the injections of Examples 12 and 13 and Reference examples 1 and 5 were administered once at 0.1 ml/kg into the cavity of the (left) knee joint having undergone operation, by using a 1 ml syringe barrel (Terumo syringe 1 ml for tuberculin, TERUMO CORPORATION) and a 23 G injection needle (Terumo injection needle 23 G, TERUMO CORPORATION). The dose of the injection administered was individually calculated by being converted into the amount of the injection based on the weight measured on the date of administration.

<Method of Measuring Pain Suppression Effect>

For measuring the weight distribution in both hindlimbs, Incapacitance Tester (manufactured by Linton Instrument UK) as an analgesic potency evaluation device for small animals was used. This device accurately detects the weight distributed to the left and right legs of the animal put in the main container, by using a dual-channel sensor pad disposed at the bottom of the container, by means of measuring the weight of each of the left and right legs in grams. The thus obtained values were averaged based on the time set by a tester. As the main container, a container for rabbit was used, and the time set for measurement was set to 5 seconds in a state where the animal stopped.

The animal was transferred into the main container (holder) for rabbit, and the measurement was performed in a state where the animal stopped (first measurement). Thereafter, the animal was taken out of the holder and then put in the holder again, and the measurement was performed in a state where the animal stopped (second measurement). This operation was repeated again (third measurement). Regarding the respective weight distribution in both hindlimbs measured three times, a proportion of the weight distributed to the left hindlimb (%) was calculated from the weight (load) on left and right hindlimbs by the following Formula (6).

Proportion of weight distributed to left hindlimb
(%)={load on left $(g)$/(load on right $(g)$+load on left $(g)$)×100}  (6)

Figure 11:
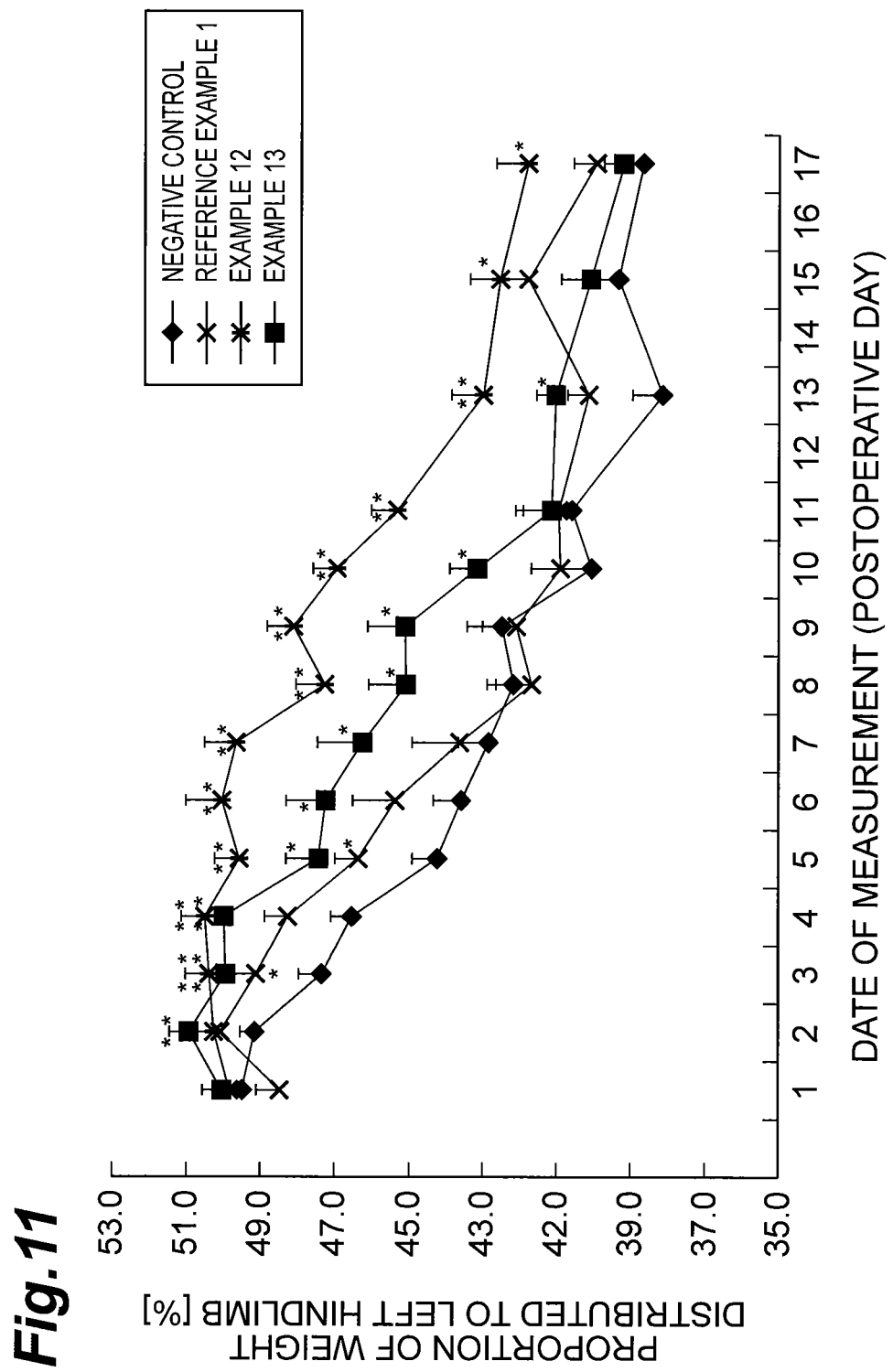
FIG. 11 is a graph showing the comparison between the crosslinked hyaluronic acid composition according to the second embodiment of the invention and the hyaluronic acid formulations as reference examples, in terms of a pain suppression effect.
Figure 12:
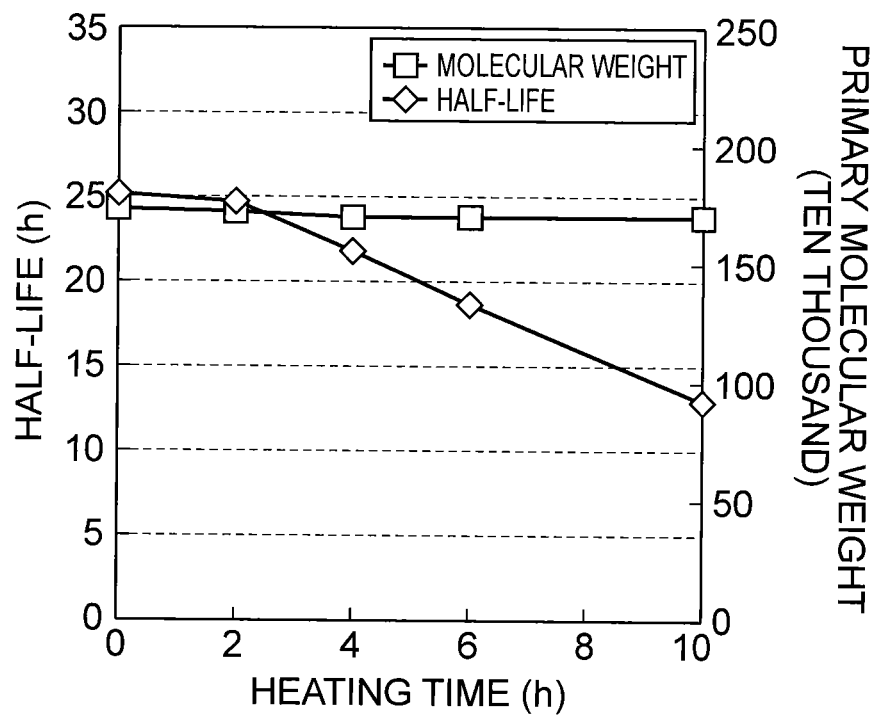
FIG. 12 is a graph showing the change in a half-life and a primary molecular weight over heating time of self-crosslinking hyaluronic acid particles according to the second embodiment.
Figure 13:
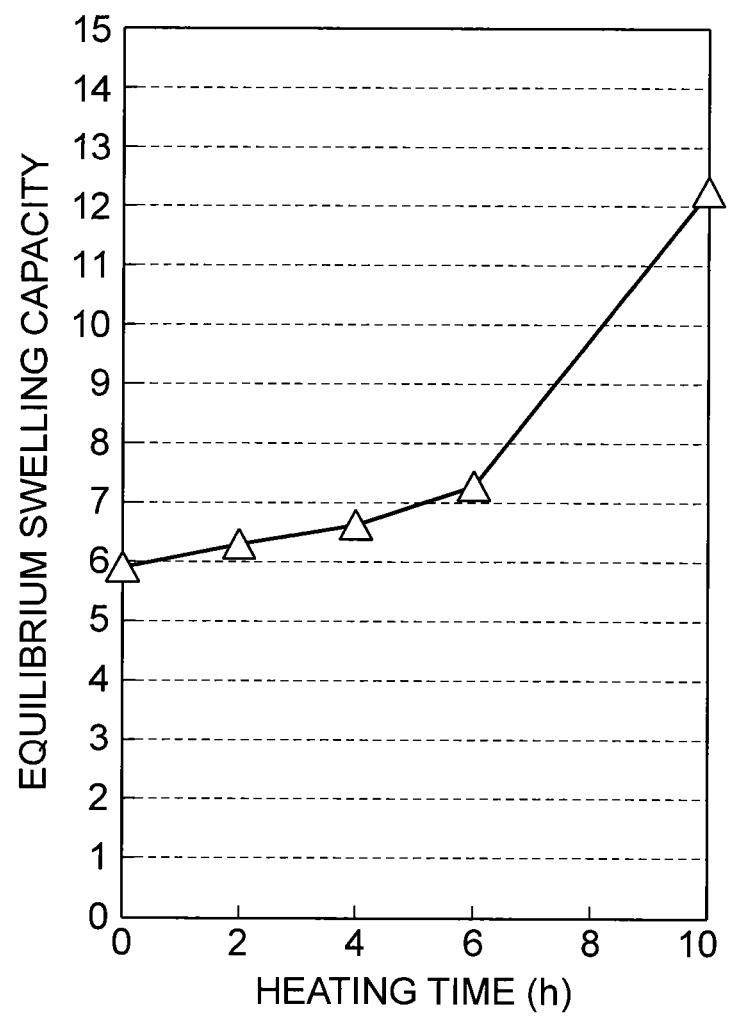
FIG. 13 is a graph showing the change in an equilibrium swelling capacity over heating time of the self-crosslinking hyaluronic acid particles according to the second embodiment.
Figure 14:
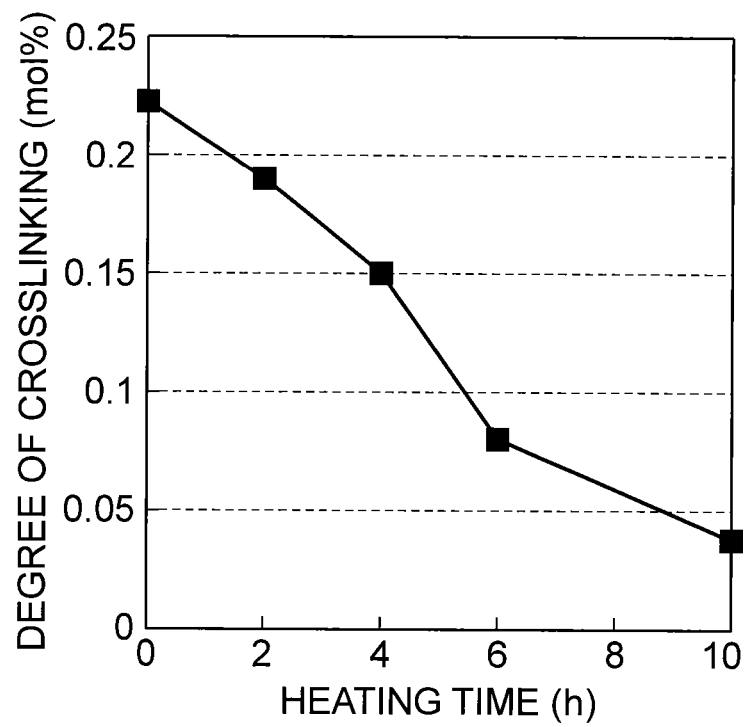
FIG. 14 is a graph showing the change in a degree of crosslinking over heating time of the self-crosslinking hyaluronic acid particles according to the second embodiment.
Figure 15:
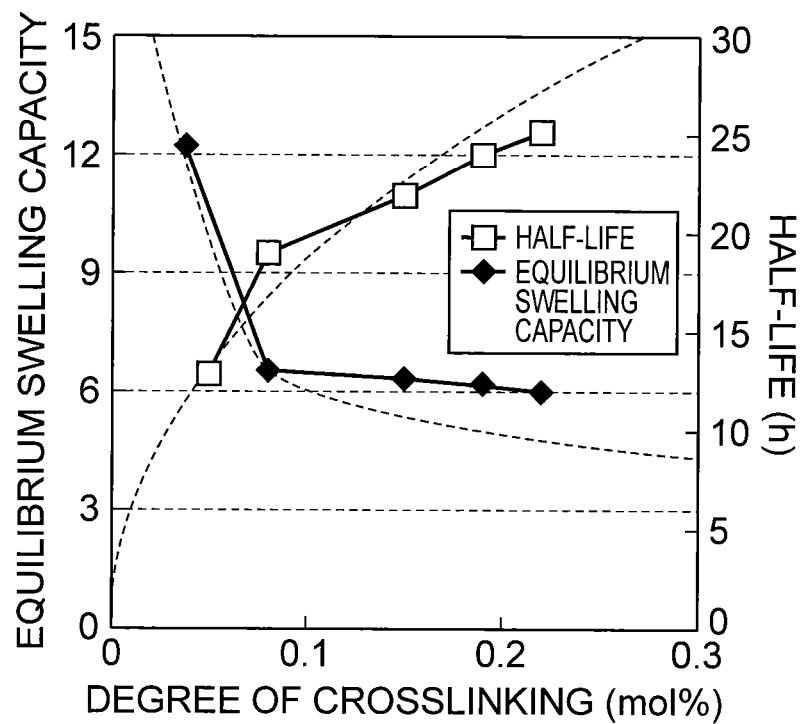
FIG. 15 is a graph showing the change in an equilibrium swelling capacity and a half-life with a degree of crosslinking of the self-crosslinking hyaluronic acid particles according to the second embodiment.

An average of the proportion of the weight distributed to the left hindlimb (%) that was calculated three times was defined as a proportion of the weight distributed to the left hindlimb (%) per measurement. As a result, as shown in FIG. 11, it was understood that the self-crosslinking hyaluronic acid of Examples 12 and 13 exhibits the improvement in the pain suppression effect compared to Reference example 1. In addition, in FIG. 11, * and ** mean that there is a significant difference between a group and a negative control (group administered with physiological saline) as Reference example 5 (*: $p<0.05$, **: $p<0.01$ (t-test)).

<Preparation of Self-Crosslinking Hyaluronic Acid Having Various Types of Degree of Self-Crosslinking Esterification>

The solvent of the self-crosslinking hyaluron obtained in Example 10 was replaced with 50 mM phosphate-buffered physiological saline (pH 7.4), thereby preparing 6 wt % of a suspension-like crosslinked hyaluronic acid composition. 7 ml of the obtained crosslinked hyaluronic acid composition was collected and transferred to a container and sealed. The crosslinked hyaluronic acid composition was repeatedly collected in the same manner, thereby obtaining 5 test samples.

The 5 test samples were put in a testing machine of a constant temperature environment (manufactured by ESPEC CORP) set to 60° C. and heated for a preset time. The five test samples were heated for different heating time. That is, at each point time when 0, 2, 4, 6, and 10 hours elapsed after the beginning of heating, the test samples were taken out one by one. By the above process, five types of crosslinked hyaluronic acid compositions were obtained. These were named Examples 14 to 17 and Comparative example 12, in the ascending order of the heating time.

<Measurement of Equilibrium Swelling Capacity>

0.4 ml of the crosslinked hyaluronic acid composition was subjected to centrifugation for 30 minutes at 5° C. and 2,000 rpm by using a centrifugal filter unit (a pore diameter of 0.45 μm, manufactured by Millipore Corporation), thereby removing the solvent. Moreover, each centrifugal filter unit was dried for 20 hours to obtain the weight of the self-crosslinking hyaluronic acid from which the solvent had been removed and the weight of the dried self-crosslinking hyaluronic acid, thereby calculating the equilibrium swelling capacity. 10 mM phosphate-buffered physiological saline (pH 6.0) was used as a solvent, and the NaCl concentration was 0.9 wt %. After the composition reached the equilibrium swelling state by being caused to swell for 1 day at 5° C., the equilibrium swelling capacity was measured.

<Measurement of Half-Life of Solubility at 60° C.>

The crosslinked hyaluronic acid compositions of Examples 14 to 17 and Comparative example 12 were measured in terms of the half-life of solubility at 60° C., in the same manner as the measurement methods in Examples 10 and 11 and Comparative examples 7 and 8.

<Measurement of Primary Molecular Weight>

As the primary molecular weight of the crosslinked hyaluronic acid compositions of Examples 14 to 17 and Comparative example 12, the viscosity average molecular weight was measured in the same manner as the measurement method in Examples 10 and 11 and Comparative examples 7 and 8.

<Measurement of Degree of Crosslinking (Degree of Self-Crosslinking Esterification)>

The crosslinked hyaluronic acid compositions of Examples 14 to 17 and Comparative example 12 were measured in terms of a degree of crosslinking (degree of self-crosslinking esterification), in the same manner as in measurement method in Examples 10 and 11 and Comparative examples 7 and 8. In addition, the measurement conditions were as follows. Instrument: AVANCEIII 500, observation width: 500.232 MHz, pulse width: 10.5 μs (90°), measurement mode: 13 C decoupling-1 H non-decoupling method, number of times of integration: 7,600 times, measurement temperature: 30° C.

The measurement results of the crosslinked hyaluronic acid compositions of Examples 14 to 17 and Comparative example 12 are shown in Table 19 and FIGS. 12 to 15.

TABLE 19

| | Heating time (h) | Degree of crosslinking (mol %) | Primary molecular weight (ten thousand) | Half-life of solubility at 60° C. (h) | Equilibrium swelling capacity |
|---|---|---|---|---|---|
| Example 14 | 0 | 0.22 | 170 | 25 | 5.9 |
| Example 15 | 2 | 0.19 | 170 | 24 | 6.2 |
| Example 16 | 4 | 0.15 | 170 | 22 | 6.6 |
| Example 17 | 6 | 0.08 | 170 | 19 | 7.3 |
| Comparative example 12 | 10 | 0.04 | 170 | 13 | 12.3 |

As shown in Table 19 and FIGS. 12 to 15, in the crosslinked hyaluronic acid compositions of which the degree of crosslinking was reduced by increasing the heating time, the half-life of solubility at 60° C. was also shortened, which showed the correlation of a quadratic function. On the other hand, the equilibrium swelling capacity increased as much as that of the crosslinked hyaluronic acid compositions of which the degree of crosslinking was reduced, and this showed the correlation similar to the Flory-Rehner equation.

<Evaluation of Storage Stability>

The solvent of the crosslinked hyaluronic acid compositions of Examples 14 to 17 and Comparative example 12 was replaced with 10 mM phosphate-buffered physiological saline (pH 6.0) so as to adjust the concentration of the self-crosslinking hyaluronic acid to 6 w/v %. Collection of samples was performed at an appropriate interval during heating in an environment at 60° C., and the amount of hyaluronic acid released was measured, thereby measuring the gel fraction. The behavior of the gel fraction with respect to the heating time was read, and the heating time taken for reaching a gel fraction of 97% was obtained. Moreover, the heating time taken for reaching a gel fraction of 95% was also obtained in the same manner as above. The measurement results are shown in the following Table 20 and FIGS. 16 and 17.

TABLE 20

|  | Heating time (h) | Value of physical properties | | | Number of days taken for reaching gel fraction | |
|---|---|---|---|---|---|---|
|  |  | Primary molecular weight (ten thousand) | Half-life of solubility at 60° C. (h) | Degree of crosslinking (mol %) | Based on 97% (day) | Based on 95% (day) |
| Example 14 | 0 | 170 | 25 | 0.22 | 3.9 | 5.0 |
| Example 15 | 2 | 170 | 24 | 0.19 | 2.9 | 4.2 |
| Example 16 | 4 | 170 | 22 | 0.15 | 2.1 | 2.9 |
| Example 17 | 6 | 170 | 19 | 0.08 | 1.3 | 2.3 |
| Comparative example 12 | 10 | 170 | 13 | 0.04 | 0.7 | 1.1 |

Figure 16:
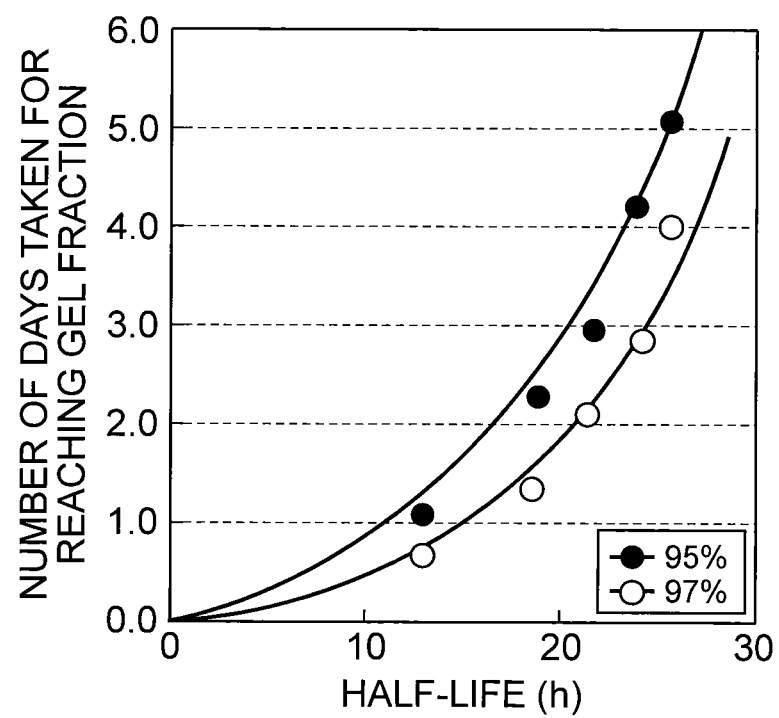
FIG. 16 is a graph showing the change in the number of days taken for reaching a gel fraction with a half-life of the self-crosslinking hyaluronic acid particles according to the second embodiment.
Figure 17:
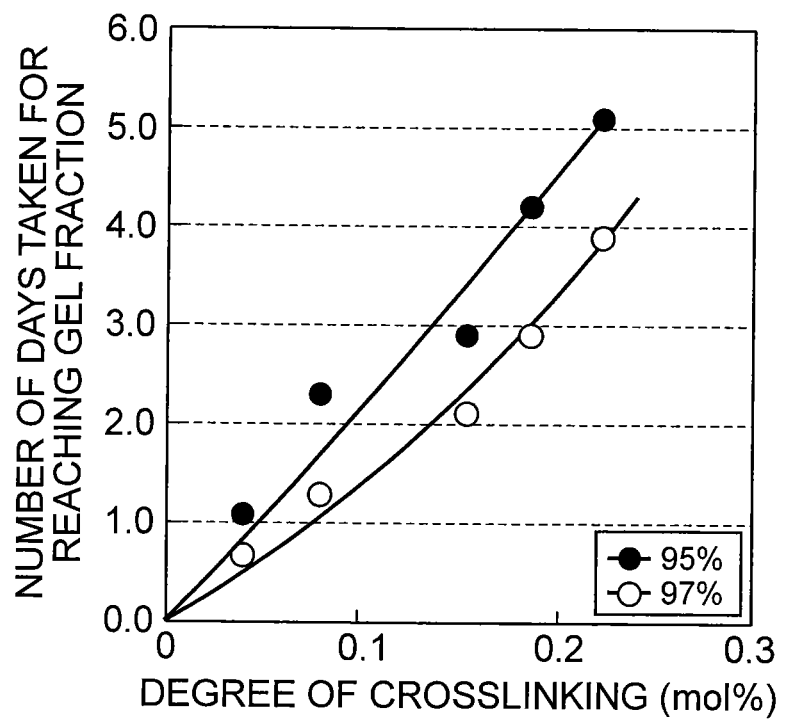
FIG. 17 is a graph showing the change in the number of days taken for reaching a gel fraction with a degree of crosslinking of the self-crosslinking hyaluronic acid particles according to the second embodiment.

As shown in Table 20, as the heating time increased, the number of days taken for reaching a gel fraction decreased. Particularly, in Comparative example 12, the heating time taken for reaching a gel fraction of 97% was reduced to 0.7 days, and the heating time taken for reaching a gel fraction of 95% was reduced to 1.1 days. In addition, as the half-life and the degree of crosslinking decreased, the number of days taken for reaching a gel fraction also decreased, and this showed that the value of these physical properties is correlated with the storage stability (FIGS. 16 and 17).

(Measurement of Average Sedimentation Concentration)

Further, the crosslinked hyaluronic acid suspensions of Examples 14 to 17 and Comparative example 12 were measured in terms of the average sedimentation concentration. The average sedimentation concentration was obtained by the following Formula (7), by measuring a hyaluronic acid concentration [C] of the suspension, a volume [$V_0$] of the suspension, and the volume [V] of the precipitate.

$$\text{Average sedimentation concentration} = C \times (V_0/V) \quad (7)$$

The measurement results are shown in the following Table 21.

TABLE 21

|  | Heating time (h) | Average sedimentation concentration (% by weight) |
|---|---|---|
| Example 14 | 0 | 11.3 |
| Example 15 | 2 | 10.9 |
| Example 16 | 4 | 8.8 |
| Example 17 | 6 | 8.1 |
| Comparative example 12 | 10 | 5.2 |

As shown in Table 21, the average sedimentation concentration as a settable upper limit of the concentration was correlated with the heating time. Particularly, Comparative example 12 had a low average sedimentation concentration such as 5.2% by weight, and this showed that the concentration cannot be increased to be as high as that of Examples 14 to 17.

INDUSTRIAL APPLICABILITY

According to the invention, it is possible to provide a crosslinked hyaluronic acid composition which can produce a sufficient curative effect on knee osteoarthritis even if the frequency of administration thereof is reduced compared to the related art, and self-crosslinking hyaluronic acid particles used for the composition.

REFERENCE SIGNS LIST

1 . . . rotor, 2 . . . screen, 3 . . . slit, 10 . . . rotation device

The invention claimed is:

1. A crosslinked hyaluronic acid composition, comprising:
self-crosslinked hyaluronic acid particles having an equilibrium swelling capacity of 3-fold to 10-fold; and
an aqueous solvent,
wherein
an ethyl ester content of the self-crosslinked hyaluronic acid particles is 0.05 mol % or less,
a degree of self-crosslinked esterification of the self-crosslinked hyaluronic acid particles is 0.05 mol % to 0.30 mol %, and
a dry weight of the self-crosslinked hyaluronic acid particles based on the total volume of the crosslinked hyaluronic acid composition is 3 w/v % to 8 w/v %.

2. The crosslinked hyaluronic acid composition according to claim 1, wherein the self-crosslinked hyaluronic acid particles have an average volume particle size of 10 μm to 100 μm.

3. The crosslinked hyaluronic acid composition according to claim 2, wherein the self-crosslinked hyaluronic acid particles have a primary molecular weight of 800,000 or more.

4. The crosslinked hyaluronic acid composition according to claim 1, wherein the ethyl ester content is 0.03 mol % or less.

5. The crosslinked hyaluronic acid composition according to claim 4, wherein the self-crosslinked hyaluronic acid particles have a primary molecular weight of 800,000 or more.

6. The crosslinked hyaluronic acid composition according to claim 1, wherein the degree of self-crosslinked esterification is from 0.08 mol % to 0.30 mol %.

7. An injection, comprising the crosslinked hyaluronic acid composition according to claim 1.

8. The injection according to claim 7, comprising 1.25 mg/kg body weight or higher of the self-crosslinked hyaluronic acid composition per administration.

9. The injection according to claim 7, comprising 75 mg or more of the self-crosslinked hyaluronic acid composition per administration.

10. A prefilled syringe formulation, comprising the injection according to claim 7.

11. Self-crosslinked hyaluronic acid particles having an average volume particle size of 10 μm to 100 μm and an equilibrium swelling capacity of 3-fold to 10-fold, wherein
an ethyl ester content of the self-crosslinked hyaluronic acid particles is 0.05 mol % or less and a degree of self-crosslinked esterification of the self-crosslinked hyaluronic acid particles is 0.05 mol % to 0.30 mol %.

12. The self-crosslinked hyaluronic acid particles according to claim 11, which have a primary molecular weight of 800,000 or more.

13. The self-crosslinked hyaluronic acid particles of claim 11, wherein the ethyl ester amount is of 0.03 mol % or less and the degree of self-crosslinked esterification is 0.08 mol % to 0.3 mol %.

14. The self-crosslinked hyaluronic acid particles according to claim 13, which have a primary molecular weight of 800,000 or more.

* * * * *